(12) United States Patent
Sanchez et al.

(10) Patent No.: US 10,584,039 B2
(45) Date of Patent: Mar. 10, 2020

(54) TITANIUM-CONTAINING FILM FORMING COMPOSITIONS FOR VAPOR DEPOSITION OF TITANIUM-CONTAINING FILMS

(71) Applicant: L'Air Liquide, Société Anonyme pour l'Etude et l'Exploitation des Procédés Georges Claude, Paris (FR)

(72) Inventors: Antonio Sanchez, Tsukuba (JP); Jean-Marc Girard, Versailles (FR); Grigory Nikiforov, Bridgewater, NJ (US); Nicolas Blasco, Echirolles (FR)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 85 days.

(21) Appl. No.: 15/827,783

(22) Filed: Nov. 30, 2017

(65) Prior Publication Data
US 2019/0161358 A1    May 30, 2019

(51) Int. Cl.
| C23C 16/08 | (2006.01) |
| C23C 16/30 | (2006.01) |
| C01G 23/02 | (2006.01) |
| C23C 16/40 | (2006.01) |
| C23C 16/34 | (2006.01) |

(Continued)

(52) U.S. Cl.
CPC ........... *C01G 23/02* (2013.01); *C01G 23/022* (2013.01); *C23C 16/34* (2013.01); *C23C 16/405* (2013.01); *C23C 16/4481* (2013.01); *C23C 16/4483* (2013.01); *C23C 16/45553* (2013.01); *H01L 21/0228* (2013.01); *H01L 21/02186* (2013.01); *H01L 21/02274* (2013.01); *H01L 21/76876* (2013.01); *C01B 7/135* (2013.01); *C07F 11/00* (2013.01); *G01N 25/4866* (2013.01); *G01R 33/46* (2013.01)

(58) Field of Classification Search
CPC ......... C23C 16/34; C23C 16/40; C23C 16/08; C23C 16/30; C23C 16/301; C01G 23/02; H01L 21/02; H01L 21/768
See application file for complete search history.

(56) References Cited

U.S. PATENT DOCUMENTS

| 3,972,862 A * | 8/1976 | Tornqvist | ............... C08F 236/06 |
| | | | 526/122 |
| 5,425,966 A * | 6/1995 | Winter | .................. C23C 16/305 |
| | | | 427/248.1 |

(Continued)

FOREIGN PATENT DOCUMENTS

FR          2 871 292        12/2005

OTHER PUBLICATIONS

Kukli, Kaupo, et al., "Atomic Layer Deposition of Titanium Oxide from TiI4 and H2O2". Chemical Vapor Deposition, 2000, 6, No. 6, pp. 303-310.*

(Continued)

*Primary Examiner* — Bret P Chen
(74) *Attorney, Agent, or Firm* — Allen E. White; Patricia E. McQueeney

(57) ABSTRACT

Titanium-containing film forming compositions comprising titanium halide-containing precursors are disclosed. Also disclosed are methods of synthesizing and using the disclosed precursors to deposit Titanium-containing films on one or more substrates via vapor deposition processes.

17 Claims, 9 Drawing Sheets

(51) Int. Cl.
*H01L 21/768* (2006.01)
*H01L 21/02* (2006.01)
*C23C 16/448* (2006.01)
*C23C 16/455* (2006.01)
*C07F 11/00* (2006.01)
*G01N 25/48* (2006.01)
*G01R 33/46* (2006.01)
*C01B 7/13* (2006.01)

(56) References Cited

U.S. PATENT DOCUMENTS

| | | | | |
|---|---|---|---|---|
| 5,595,784 | A * | 1/1997 | Kaim | C23C 16/14 257/E21.584 |
| 5,656,338 | A | 8/1997 | Gordon | |
| 6,255,204 | B1 * | 7/2001 | Tobin | H01L 21/28079 257/E21.202 |
| 6,706,115 | B2 | 3/2004 | Leskela et al. | |
| 2002/0013050 | A1 * | 1/2002 | Sharan | C23C 16/14 438/680 |
| 2003/0124842 | A1 * | 7/2003 | Hytros | C23C 16/34 438/680 |
| 2003/0153841 | A1 * | 8/2003 | Kilborn | A61B 5/0484 600/544 |
| 2005/0042888 | A1 | 2/2005 | Roeder et al. | |
| 2009/0247804 | A1 * | 10/2009 | Sauer | B01J 27/125 585/733 |
| 2010/0104755 | A1 | 4/2010 | Dussarrat et al. | |
| 2011/0198736 | A1 | 8/2011 | Shero et al. | |
| 2014/0174955 | A1 * | 6/2014 | Sasagawa | F17C 1/00 206/0.6 |
| 2014/0208968 | A1 * | 7/2014 | Shibusawa | B41N 1/247 101/395 |
| 2016/0293410 | A1 * | 10/2016 | Lei | C07F 5/022 |
| 2017/0170114 | A1 * | 6/2017 | Besser | C22C 14/00 |
| 2019/0161507 | A1 * | 5/2019 | Sanchez | C07F 7/28 |

OTHER PUBLICATIONS

Gordon, Roy G., "Overview of ALD Precursors and Reaction Mechanisms". Tutorial for ALD, 2011, Harvard University, pp. 1-67.*
Liu, Zhang, et al., "Low-Temperature Reverse Microemulsion Synthesis, Characterization, and Photocatalytic Performance of Nanocrystalline Titanium Dioxide". International Journal of Photoenergy, vol. 20212, Article ID 702503, 8 pages.*
Sakai, Toshio, et al., "Formation Mechanism for Hexagonal-Structured Self-Assemblies of Nanocrytalline Titania Templated by Cetyltrimethylammonium Bromide". Journal of Oleo Science, 57 (11) 629-637 (2008).*
Qin, Jiangiang, et al., "The optimum titanium precursor of fabricating TiO2 compact layer for perovskite solar cells". Nanoscale Research Letters (2017) 12:640, pp. 1-9.*
Leskela, Markku, et al., "Atomic Layer Deposition (ALD): from precursors to thin film structures". Thin Solid Films 409 (2002) 138-146.*

Gayer, Karl H., et al., "The Low Temperature Preparation of Anhydrous Titanium IV Bromide and Anhydrous Titanium IV Iodide from Benzene Solutions". Canadian Journal of Chemistry, vol. 37, 1959, pp. 1373-1374.*
Dermer, O.C. et al., "Die Einwirkung von Titantetrachlorid auf organishe Stickstoffverbindungen," Zeitschrift fuer Anorganische und Allgemeine Chemie (1934) 221, 83-96.
Fenske, D. et al., "N,N'-bis(trimethylsilyl)benzamidinato-Komplexe von Titan und Zirkon. Die Kristallstrukturen von [$C_6H$—$C(NSiMe_3)_2MCl_3$]2; M = Ti, Zr," Z. Naturforsch, Jun. 22, 1988, 43b, 1611-1615, English abstract.
Liguori, D. et al., "Titanium monoamidinate-MAO catalysts: some information about active species and stereochemical polymerization mechanisms," Macromolecules 2003, 36, 5451-5458.
International Search Report and Written Opinion for corresponding PCT/US2018/058084, dated Feb. 5, 2019.
Baker, K. et al., "Sulphur complexes of quadrivalent titanium," J. Less-Common Metals, 1964, 47-50.
Benjamin, S.L. et al., "Niobium(V) and tantalum(V) halide chalcogenoether complexes—towards single source CVD precursors for $ME_2$ thin films," Royal Society of Chemistry, Dalton Transactions, 2014, 43, 16640-16648.
Bürger, H. et al., "Cyclic titanium amides with sila-titanadiazacyclobutane structure," Zeitschrift für Anorganische und Allgemeine Chemie, 459, 1979, 111-118, English Abstract.
Bürger, H. et al., "Dialkylamido-titanfluoride," Zeitschrift für Anorganische und Allgemeine Chemie, 898, 1973, 257-272, English Abstract.
Bürger, H. et al., "Dialkylamido-titanjodide," Zeitschrift für Anorganische und Allgemeine Chemie, Band 381, 1971, 198-204, English Abstract.
Bürger, H. et al., "Dialkylamino-titanbromide," Zeitschrift für Anorganische und Allgemeine Chemie, Band 370, 1969, 275-282, English Abstract.
Emeleus, H.J. et al., "Complexes of titanium and zirconium halides with organic ligands," J. Chemical Society (Resumed), 1958, 4245-4250.
Fowles, G.W.A. et al., "The reaction between ammonia and transition-metal halides. Part V. The reaction of ammonia with titanium(IV) bromide and titanium (IV) iodide," J. Chemical Society (Resumed), 1959, 990-997.
Fowles, G.W.A. et al., "The reaction of titanium halides with tertiary amines," J. Chemical Society (Resumed), 1963, 33-38.
Herzog, A. et al., "Trimethyltin fluoride: a new fluorinating reagent for the preparation of organometallic fluorides," Organometallics 1994, 13, 1251-1256.
Höltje, R., Über Anlagerungsverbindungen des Phosphorwasserstoffs, Zeitschrift fuer Anorganische und Allgemeine Chemie, 1930, 190, 241-256.
Muetterties, E.L., "Stereochemistry of complexes based on metal tetrafluorides," 1960, vol. 82, No. 5, 1082-1087.
Nikiforov, G.B. et al., "A survey of titanium fluoride complexes, their preparation, reactivity, and applications," Coordination Chemistry Reviews 258-259 (2014) 16-57.
Ruff, O. et al., "Ober neue Titan-Verbindungen (Titanstickstoff u.a.)," Berichte der Deutschen Chemischen Gesellschaft, 1912, 45, 1364-1373.
Turin, E. et al., "Adducts of titanium tetrahalides with neutral Lewis bases. Part I. Structure and stability: a vibrational and multinuclear NMR study," Inorganica Chimica Acta, 134 (1987), 67-78.

* cited by examiner

TITANIUM-CONTAINING FILM FORMING COMPOSITIONS FOR VAPOR DEPOSITION OF TITANIUM-CONTAINING FILMS

TECHNICAL FIELD

Disclosed are Ti-containing film forming compositions comprising titanium halide-containing precursors. Also disclosed are methods of synthesizing and using the disclosed precursors to deposit titanium-containing films on one or more substrates via vapor deposition processes.

BACKGROUND

With the scaling down of semiconductor devices, new materials with high dielectric constant are required. Chemical Vapor Deposition (CVD) and Atomic Layer Deposition (ALD) have become the main deposition techniques for such thin films. CVD and ALD may provide different films (metal, oxide, nitride, etc.) having a finely defined thickness and high step coverage. In CVD and ALD, the precursor molecule plays a critical role to obtain high quality films with high conformality and low impurities.

Among high-k dielectrics, titanium based materials, such as $TiO_2$, are very promising, whether used as pure or mixed oxides or in laminates. TiN may be used for electrode and/or Cu diffusion barrier applications. Titanium oxides may also be used for their etch resistance properties in lithography applications, such as for hard masks or spacer-defined multiple patterning applications. Titanium silicides may serves as a contact between conductive plugs and the underlying doped silicon layer.

Synthesis and characterization of a variety of titanium halide Lewis adducts is known. See, e.g., Ruff et al., New titanium compounds, Berichte der Deutschen Chemischen Gesellschaft, 1912, 45, pp. 1364-1373;
R. Höltje, Zeitschrift fuer Anorganische and Allgemeine Chemie, 1930, 190, pp 241-256;
Emeléus et al., Complexes of Titanium and Zirconium Halides with Organic Ligands, J. Chemical Society (Resumed), 1958, pp. 4245-50;
Fowles et al., Journal of Chemical Society (Resumed), 1959 pp. 990-997;
G. W. A. Fowles et al., The Reaction of Titanium Halides with Tertiary Amines, Journal of Chemical Society (Resumed), 1963, pp. 33-38;
Baker et al., Sulphur Complexes of Quadrivalent Titanium, Journal of the Less-Common Metals, 1964, pp. 47-50;
Eric Turin et al., Adducts of Titanium Tetrahalides with Neutral Lewis Bases.
Part I. Structure and Stability: a Vibrational and Multinuclear NMR Study, Inorganica Chimica Acta, 134 (1987) pp. 67-78;
U.S. Pat. No. 5,656,338 to Gordon discloses chemical vapor deposition of titanium metal by forming a liquid solution of titanium tetrabromide in bromine, vaporizing the solution and contacting the vapor mixture with plasma in the vicinity of the substrate;
U.S. Pat. No. 6,706,115 to Leskelä et al. discloses methods for producing metal nitride thin layers have low resistivity by means of atomic layer deposition processes comprising alternate surface reactions of metal and nitrogen source materials; and
U.S. Pat. App. Pub. No. 2010/0104755 to Dussarrat et al. discloses methods for producing a metal-containing film by introducing a metal source which does not contain metal-C or metal-N—C s-bonds, a silicon precursor, a nitrogen precursor, a carbon source and a reducing agent into a CVD chamber and reacting same at the surface of a substrate to produce a metal containing film in a single step.

Synthesis and characterization of a variety of mixed titanium halo alkylamino derivatives is also known. See, e.g., Von Hans Bürger et al., Dialkylamino-titanbromide, Zeitschrift für anorganische und allgemeine Chemie, Band 370, 1969, pp. 275-282;
Von Hans Bürger et al., Dialkylamido-titaniodide, Zeitschrift für anorganishce und allgemeine Chemie, Band 381, 1971, pp. 198-204;
US Pat App Pub No. 2005/0042888 to Roder et al. discloses metalorganic precursors of the formula $(R_1R_2N)_{a-b}MX_b$, wherein M is the precursor metal center, selected form the group of Ta, Ti, W, Nb, Si, Al, and B; a is a number equal to the valence of M; $1 \le b \le (a-1)$; $R_1$ and $R_2$ can be the same as or different from one another and are each independently selected from the group of H, C1-C4 alkyl, C3-C6 cycloalkyl, and $R°_3Si$, where each $R°$ can be the same or different and each $R°$ is independently selected from H and C1-C4 alkyl; and X is selected from the group of chlorine, fluorine, bromine and iodine.

FR Pat. App. Pub. No. 2871292 to Dussarrat discloses injection of a metallic precursor having the formula $MX_4$ or $MX_5$, wherein M is preferably Hf, an oxidant and of tetrakis(ethylamino)silane under temperature and pressure conditions that improve the reactivity of the silicon source.

A need remains for thermally stable, volatile, and preferably liquid Ti-containing precursors capable of providing controlled film thickness during vapor phase deposition at high temperature.

SUMMARY

Ti-containing film forming compositions are disclosed comprising Ti halide-containing precursors having one of the following formula:

$TiX_b:A_c$ with b=3 or 4; c=1-3; X=Br or I; $A=SR_2$, $SeR_2$, $TeR_2$, or $PR_3$, and each R is independently H or a C1-C10 hydrocarbon.

Also disclosed are Ti-containing film forming compositions comprising Ti halide-containing precursors having one of the following formula:

$Ti(NR'_2)_y(X)_z$

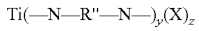
$Ti(-N-R''-N-)_y(X)_z$ with y=1-3; z=1-3; y+z=4; X=Br or I; each R' independently a C1-C5 hydrocarbon or $SiR'''_3$, with each R''' independently being H or a C1-C5 hydrocarbon; and R''=a C1-C5 hydrocarbon.

Any of the disclosed Ti-containing film forming compositions may further include one or more of the following aspects:
- each R independently being a C1-C5 hydrocarbon;
- b=4 when c=1 or 2;
- b=3 when c=3;
- the Ti halide-containing precursor having a melting point lower than the melting point of the analogous $TiX_4$ compound;
- X is Br;
- the Ti halide-containing precursor having a melting point between approximately −50° C. and approximately 39° C. at standard pressure;

X is I;
the Ti halide-containing precursor having a melting point between approximately −50° C. and approximately 150° C. at standard pressure;
the Ti halide-containing precursor having a melting point between approximately −50° C. and approximately 30° C. at standard pressure;
the Ti halide-containing precursor being a liquid at standard temperature and pressure;
A is $SR_2$, with each R independently a C1-C5 hydrocarbon;
A is $SPr_2$;
A is $SBu_2$;
A is tetrahydrothiophene;
A=$SR_2$, c=1, and each R is independently a C3-C5 hydrocarbon;
A=$SR_2$, c=2, and each R is independently a C1-2 hydrocarbon;
A=tetrahydrothiophene and c=2;
the Ti halide-containing precursor being $TiBr_4$:$SEt_2$;
the Ti halide-containing precursor being $TiBr_4$:$S(nPr)_2$;
the Ti halide-containing precursor being $TiBr_4$:$S(iPr)_2$;
the Ti halide-containing precursor being $TiBr_4$:$SBu_2$;
the Ti halide-containing precursor being $TiBr_4$:$S(nBu)_2$;
the Ti halide-containing precursor being $TiBr_4$:$S(tBu)_2$;
the Ti halide-containing precursor being $TiBr_4$:$S(iBu)_2$;
the Ti halide-containing precursor being $TiBr_4$:$S(sBu)_2$;
the Ti halide-containing precursor being $TiBr_4$:$(SEt_2)_2$;
the Ti halide-containing precursor being $TiBr_4$:$(SMe_2)_2$;
the Ti halide-containing precursor being $TiBr_4$:$(SMeEt)_2$;
the Ti halide-containing precursor being $TiBr_4$:(tetrahydrothiophene)$_2$;
the Ti halide-containing precursor being $TiI_4$:$SEt_2$;
the Ti halide-containing precursor being $TiI_4$:$S(nPr)_2$;
the Ti halide-containing precursor being $TiI_4$:$S(iPr)_2$;
the Ti halide-containing precursor being $TiI_4$:$SBu_2$;
the Ti halide-containing precursor being $TiI_4$:$S(nBu)_2$;
the Ti halide-containing precursor being $TiI_4$:$S(tBu)_2$;
the Ti halide-containing precursor being $TiI_4$:$S(iBu)_2$;
the Ti halide-containing precursor being $TiI_4$:$S(sBu)_2$;
the Ti halide-containing precursor being $TiI_4$:$(SEt_2)_2$;
the Ti halide-containing precursor being $TiI_4$:$(SMe_2)_2$;
the Ti halide-containing precursor being $TiI_4$:$(SMeEt)_2$;
the Ti halide-containing precursor being $TiI_4$:(tetrahydrothiophene)$_2$;
A is $SeR_2$, with each R independently a C1-C5 hydrocarbon;
A is $SePr_2$;
A is $SeBu_2$;
A is tetrahydroselenophene;
A=$SeR_2$, c=1, and each R is independently a C3-C5 hydrocarbon;
A=$SeR_2$, c=2, and each R is independently a C1-2 hydrocarbon;
A=tetrahydroselenophene and c=2;
the Ti halide-containing precursor being $TiBr_4$:$SePr_2$;
the Ti halide-containing precursor being $TiBr_4$:$SeBu_2$;
the Ti halide-containing precursor being $TiBr_4$:$(SeMe_2)_2$;
the Ti halide-containing precursor being $TiBr_4$:$(SeEt_2)_2$;
the Ti halide-containing precursor being $TiBr_4$:(SeMeEt)$_2$;
the Ti halide-containing precursor being $TiBr_4$:(tetrahydroselenophene)$_2$;
the Ti halide-containing precursor being $TiI_4$:$SePr_2$;
the Ti halide-containing precursor being $TiI_4$:$SeBu_2$;
the Ti halide-containing precursor being $TiI_4$:$(SeMe_2)_2$;
the Ti halide-containing precursor being $TiI_4$:$(SeEt_2)_2$;
the Ti halide-containing precursor being $TiI_4$:$(SeMeEt)_2$;
the Ti halide-containing precursor being $TiI_4$:(tetrahydroselenophene)$_2$;
L is $TeR_2$, with each R independently a C1-C5 hydrocarbon;
A is $TePr_2$;
A is $TeBu_2$;
A is tetrahydrotellurophene;
A=$TeR_2$, c=1, with each R independently a C3-C5 hydrocarbon;
A=$TeR_2$, c=2, with each R independently a C1-2 hydrocarbon;
A=tetrahydrotellurophene and c=2;
the Ti halide-containing precursor being $TiBr_4$:$TePr_2$;
the Ti halide-containing precursor being $TiBr_4$:$TeBu_2$;
the Ti halide-containing precursor being $TiBr_4$:$(TeMe_2)_2$;
the Ti halide-containing precursor being $TiBr_4$:$(TeEt_2)_2$;
the Ti halide-containing precursor being $TiBr_4$:$(TeMeEt)_2$;
the Ti halide-containing precursor being $TiBr_4$:(tetrahydrotellurophene)$_2$;
the Ti halide-containing precursor being $TiI_4$:$TePr_2$;
the Ti halide-containing precursor being $TiI_4$:$TeBu_2$;
the Ti halide-containing precursor being $TiI_4$:$(TeMe_2)_2$;
the Ti halide-containing precursor being $TiI_4$:$(TeEt_2)_2$;
the Ti halide-containing precursor being $TiI_4$:$(TeMeEt)_2$;
the Ti halide-containing precursor being $TiI_4$:(tetrahydrotellurophene)$_2$;
A is $PR_3$, with each R independently H or a C1-C5 hydrocarbon;
the Ti halide-containing precursor being $TiBr_4$:$PR_3$, with each R independently H or a C3-C10 hydrocarbon;
the Ti halide-containing precursor being $TiBr_4$:$PH_3$;
the Ti halide-containing precursor being $TiBr_4$:$(PR_3)_2$, with each R independently H or a C1-2 hydrocarbon;
the Ti halide-containing precursor being $TiBr_4$:$(PH_3)_2$;
the Ti halide-containing precursor being $TiBr_3$:$(PR_3)_3$, with each R independently H or a C1-2 hydrocarbon;
the Ti halide-containing precursor being $TiBr_3$:$(PH_3)_3$;
the Ti halide-containing precursor being $TiBr_4$:($R_2$P—$(CH_2)_n$—$PR_2$), with each R independently a C1-5 hydrocarbon and n=1-4;
the Ti halide-containing precursor being $TiBr_4$:($Me_2$P—$(CH_2)_n$—$PMe_2$);
the Ti halide-containing precursor being $TiBr_4$:(EtMeP—$(CH_2)_n$—PMeEt);
the Ti halide-containing precursor being $TiBr_4$:($Et_2$P—$(CH_2)_n$—$PEt_2$);
the Ti halide-containing precursor being $TiBr_4$:($iPr_2$P—$(CH_2)_n$—$PiPr_2$);
the Ti halide-containing precursor being $TiBr_4$:(HiPrP—$(CH_2)_n$—PHiPr);
the Ti halide-containing precursor being $TiBr_4$:($tBu_2$P—$(CH_2)_n$—$PtBu_2$);
the Ti halide-containing precursor being $TiBr_4$:(tBuHP—$(CH_2)_n$—PHtBu);
the Ti halide-containing precursor being $TiBr_4$:(tAmHP—$(CH_2)_n$—PHtAm);
the Ti halide-containing precursor being $TiBr_4$:($Me_2$P—$(CH_2)$—$PMe_2$);
the Ti halide-containing precursor being $TiBr_4$:(EtMeP—$(CH_2)$—PMeEt);
the Ti halide-containing precursor being $TiBr_4$:($Et_2$P—$(CH_2)$—$PEt_2$);
the Ti halide-containing precursor being $TiBr_4$:($iPr_2$P—$(CH_2)$—$PiPr_2$);

the Ti halide-containing precursor being TiBr$_4$:(HiPrP—(CH$_2$)—PHiPr);

the Ti halide-containing precursor being TiBr$_4$:(tBu$_2$P—(CH$_2$)—PtBu$_2$);

the Ti halide-containing precursor being TiBr$_4$:(tBuHP—(CH$_2$)—PHtBu);

the Ti halide-containing precursor being TiBr$_4$:(tAmHP—(CH$_2$)—PHtAm);

the Ti halide-containing precursor being TiBr$_4$:(Me$_2$P—(CH$_2$)$_2$—PMe$_2$);

the Ti halide-containing precursor being TiBr$_4$:(EtMeP—(CH$_2$)$_2$—PMeEt);

the Ti halide-containing precursor being TiBr$_4$:(Et$_2$P—(CH$_2$)$_2$—PEt$_2$);

the Ti halide-containing precursor being TiBr$_4$:(iPr$_2$P—(CH$_2$)$_2$—PiPr$_2$);

the Ti halide-containing precursor being TiBr$_4$:(HiPrP—(CH$_2$)$_2$—PHiPr);

the Ti halide-containing precursor being TiBr$_4$:(tBu$_2$P—(CH$_2$)$_2$—PtBu$_2$);

the Ti halide-containing precursor being TiBr$_4$:(tBuHP—(CH$_2$)$_2$—PHtBu);

the Ti halide-containing precursor being TiBr$_4$:(tAmHP—(CH$_2$)$_2$—PHtAm);

the Ti halide-containing precursor being TiI$_4$:(Me$_2$P—(CH$_2$)$_n$—PMe$_2$);

the Ti halide-containing precursor being TiI$_4$:(EtMeP—(CH$_2$)$_n$—PMeEt);

the Ti halide-containing precursor being TiI$_4$:(Et$_2$P—(CH$_2$)$_n$—PEt$_2$);

the Ti halide-containing precursor being TiI$_4$:(iPr$_2$P—(CH$_2$)$_n$—PiPr$_2$);

the Ti halide-containing precursor being TiI$_4$:(HiPrP—(CH$_2$)$_n$—PHiPr);

the Ti halide-containing precursor being TiI$_4$:(tBu$_2$P—(CH$_2$)$_n$—PtBu$_2$);

the Ti halide-containing precursor being TiI$_4$:(tBuHP—(CH$_2$)$_n$—PHtBu);

the Ti halide-containing precursor being TiI$_4$:(tAmHP—(CH$_2$)$_n$—PHtAm);

the Ti halide-containing precursor being TiI$_4$:(Me$_2$P—(CH$_2$)—PMe$_2$);

the Ti halide-containing precursor being TiI$_4$:(EtMeP—(CH$_2$)—PMeEt);

the Ti halide-containing precursor being TiI$_4$:(Et$_2$P—(CH$_2$)—PEt$_2$);

the Ti halide-containing precursor being TiI$_4$:(iPr$_2$P—(CH$_2$)—PiPr$_2$);

the Ti halide-containing precursor being TiI$_4$:(HiPrP—(CH$_2$)—PHiPr);

the Ti halide-containing precursor being TiI$_4$:(tBu$_2$P—(CH$_2$)—PtBu$_2$);

the Ti halide-containing precursor being TiI$_4$:(tBuHP—(CH$_2$)—PHtBu);

the Ti halide-containing precursor being TiI$_4$:(tAmHP—(CH$_2$)—PHtAm);

the Ti halide-containing precursor being TiI$_4$:(Me$_2$P—(CH$_2$)$_2$—PMe$_2$);

the Ti halide-containing precursor being TiI$_4$:(EtMeP—(CH$_2$)$_2$—PMeEt);

the Ti halide-containing precursor being TiI$_4$:(Et$_2$P—(CH$_2$)$_2$—PEt$_2$);

the Ti halide-containing precursor being TiI$_4$:(iPr$_2$P—(CH$_2$)$_2$—PiPr$_2$);

the Ti halide-containing precursor being TiI$_4$:(HiPrP—(CH$_2$)$_2$—PHiPr);

the Ti halide-containing precursor being TiI$_4$:(tBu$_2$P—(CH$_2$)$_2$—PtBu$_2$);

the Ti halide-containing precursor being TiI$_4$:(tBuHP—(CH$_2$)$_2$—PHtBu);

the Ti halide-containing precursor being TiI$_4$:(tAmHP—(CH$_2$)$_2$—PHtAm);

the Ti halide-containing precursor being TiBr$_3$:(R$_2$P—(CH$_2$)$_n$—PR$_2$), with each R independently a C1-5 hydrocarbon and n=1-4;

the Ti halide-containing precursor being TiBr$_3$:(Me$_2$P—(CH$_2$)$_n$—PMe$_2$);

the Ti halide-containing precursor being TiBr$_3$:(EtMeP—(CH$_2$)$_n$—PMeEt);

the Ti halide-containing precursor being TiBr$_3$:(Et$_2$P—(CH$_2$)$_n$—PEt$_2$);

the Ti halide-containing precursor being TiBr$_3$:(iPr$_2$P—(CH$_2$)$_n$—PiPr$_2$);

the Ti halide-containing precursor being TiBr$_3$:(HiPrP—(CH$_2$)$_n$—PHiPr);

the Ti halide-containing precursor being TiBr$_3$:(tBu$_2$P—(CH$_2$)$_n$—PtBu$_2$);

the Ti halide-containing precursor being TiBr$_3$:(tBuHP—(CH$_2$)$_n$—PHtBu);

the Ti halide-containing precursor being TiBr$_3$:(tAmHP—(CH$_2$)$_n$—PHtAm);

the Ti halide-containing precursor being TiBr$_3$:(Me$_2$P—(CH$_2$)—PMe$_2$);

the Ti halide-containing precursor being TiBr$_3$:(EtMeP—(CH$_2$)—PMeEt);

the Ti halide-containing precursor being TiBr$_3$:(Et$_2$P—(CH$_2$)—PEt$_2$);

the Ti halide-containing precursor being TiBr$_3$:(iPr$_2$P—(CH$_2$)—PiPr$_2$);

the Ti halide-containing precursor being TiBr$_3$:(HiPrP—(CH$_2$)—PHiPr);

the Ti halide-containing precursor being TiBr$_3$:(tBu$_2$P—(CH$_2$)—PtBu$_2$);

the Ti halide-containing precursor being TiBr$_3$:(tBuHP—(CH$_2$)—PHtBu);

the Ti halide-containing precursor being TiBr$_3$:(tAmHP—(CH$_2$)—PHtAm);

the Ti halide-containing precursor being TiBr$_3$:(Me$_2$P—(CH$_2$)$_2$—PMe$_2$);

the Ti halide-containing precursor being TiBr$_3$:(EtMeP—(CH$_2$)$_2$—PMeEt);

the Ti halide-containing precursor being TiBr$_3$:(Et$_2$P—(CH$_2$)$_2$—PEt$_2$);

the Ti halide-containing precursor being TiBr$_3$:(iPr$_2$P—(CH$_2$)$_2$—PiPr$_2$);

the Ti halide-containing precursor being TiBr$_3$:(HiPrP—(CH$_2$)$_2$—PHiPr);

the Ti halide-containing precursor being TiBr$_3$:(tBu$_2$P—(CH$_2$)$_2$—PtBu$_2$);

the Ti halide-containing precursor being TiBr$_3$:(tBuHP—(CH$_2$)$_2$—PHtBu);

the Ti halide-containing precursor being TiBr$_3$:(tAmHP—(CH$_2$)$_2$—PHtAm);

the Ti halide-containing precursor being TiI$_3$:(Me$_2$P—(CH$_2$)$_n$—PMe$_2$);

the Ti halide-containing precursor being TiI$_3$:(EtMeP—(CH$_2$)$_n$—PMeEt);

the Ti halide-containing precursor being TiI$_3$:(Et$_2$P—(CH$_2$)$_n$—PEt$_2$);

the Ti halide-containing precursor being TiI$_3$:(iPr$_2$P—(CH$_2$)$_n$—PiPr$_2$);

the Ti halide-containing precursor being TiI$_3$:(HiPrP—(CH$_2$)$_n$—PHiPr);

the Ti halide-containing precursor being TiI$_3$:(tBu$_2$P—(CH$_2$)$_n$—PtBu$_2$);
the Ti halide-containing precursor being TiI$_3$:(tBuHP—(CH$_2$)$_n$—PHtBu);
the Ti halide-containing precursor being TiI$_3$:(tAmHP—(CH$_2$)$_n$—PHtAm);
the Ti halide-containing precursor being TiI$_3$:(Me$_2$P—(CH$_2$)—PMe$_2$);
the Ti halide-containing precursor being TiI$_3$:(EtMeP—(CH$_2$)—PMeEt);
the Ti halide-containing precursor being TiI$_3$:(Et$_2$P—(CH$_2$)—PEt$_2$);
the Ti halide-containing precursor being TiI$_3$:(iPr$_2$P—(CH$_2$)—PiPr$_2$);
the Ti halide-containing precursor being TiI$_3$:(HiPrP—(CH$_2$)—PHiPr);
the Ti halide-containing precursor being TiI$_3$:(tBu$_2$P—(CH$_2$)—PtBu$_2$);
the Ti halide-containing precursor being TiI$_3$:(tBuHP—(CH$_2$)—PHtBu);
the Ti halide-containing precursor being TiI$_3$:(tAmHP—(CH$_2$)—PHtAm);
the Ti halide-containing precursor being TiI$_3$:(Me$_2$P—(CH$_2$)$_2$—PMe$_2$);
the Ti halide-containing precursor being TiI$_3$:(EtMeP—(CH$_2$)$_2$—PMeEt);
the Ti halide-containing precursor being TiI$_3$:(Et$_2$P—(CH$_2$)$_2$—PEt$_2$);
the Ti halide-containing precursor being TiI$_3$:(iPr$_2$P—(CH$_2$)$_2$—PiPr$_2$);
the Ti halide-containing precursor being TiI$_3$:(HiPrP—(CH$_2$)$_2$—PHiPr);
the Ti halide-containing precursor being TiI$_3$:(tBu$_2$P—(CH$_2$)$_2$—PtBu$_2$);
the Ti halide-containing precursor being TiI$_3$:(tBuHP—(CH$_2$)$_2$—PHtBu);
the Ti halide-containing precursor being TiI$_3$:(tAmHP—(CH$_2$)$_2$—PHtAm);
A is R(=O)Cl, with R being a C2-C4 hydrocarbon;
the Ti halide-containing precursor being TiBr$_4$:R(=O)Cl, with R being a C2-C10 hydrocarbon;
the Ti halide-containing precursor being TiBr$_4$:(Me-C(=O)Cl);
the Ti halide-containing precursor being TiBr$_4$:(Ph-C(=O)Cl);
the Ti halide-containing precursor being TiI$_4$:(Me-C(=O)Cl);
A is RNO$_2$, with R being a C1-C5 hydrocarbon;
the Ti halide-containing precursor being TiBr$_4$:(MeNO$_2$);
the Ti halide-containing precursor being TiI$_4$:(MeNO$_2$);
the Ti halide-containing precursor being TiBr$_4$:(EtNO$_2$);
the Ti halide-containing precursor being TiBr$_4$:(PrNO$_2$);
the Ti halide-containing precursor being TiBr$_4$:(PhNO$_2$);
A is R≡N, with R being a C2-C6 hydrocarbon;
the Ti halide-containing precursor being TiBr$_4$:(Me-C≡N)$_2$;
the Ti halide-containing precursor being TiBr$_4$:(Et-C≡N)$_2$;
the Ti halide-containing precursor being TiBr$_4$:(Pr-C≡N)$_2$;
the Ti halide-containing precursor being TiBr$_4$:(Bu-C≡N)$_2$;
the Ti halide-containing precursor being TiBr$_4$:(Ph-C≡N)$_2$;
A is pyridine;
A is piperidine;
the Ti halide-containing precursor being TiBr$_4$:pyridine;
the Ti halide-containing precursor being TiBr$_4$:piperidine;
the Ti halide-containing precursor being TiBr$_4$:2,2,6,6-tetramethylpiperidine;
the Ti halide-containing precursor being TiX$_3$(NR$_2$);
the Ti halide-containing precursor being TiBr$_3$(NR$_2$);
the Ti halide-containing precursor being TiBr$_3$(NEt$_2$);
the Ti halide-containing precursor being TiBr$_3$(pyrrolidine);
the Ti halide-containing precursor being TiBr$_3$(pyridine);
the Ti halide-containing precursor being TiBr$_3$(piperidine);
the Ti halide-containing precursor being TiI$_3$(NR$_2$);
the Ti halide-containing precursor being TiX$_2$(NR$_2$)$_2$;
the Ti halide-containing precursor being TiBr$_2$(NR$_2$)$_2$;
the Ti halide-containing precursor being TiBr$_2$(NMe$_2$)$_2$;
the Ti halide-containing precursor being TiI$_2$(NR$_2$)$_2$;
the Ti halide-containing precursor being TiX(NR$_2$)$_3$;
the Ti halide-containing precursor being TiBr(NR$_2$)$_3$;
the Ti halide-containing precursor being TiI(NR$_2$)$_3$;
the Ti halide-containing precursor being TiX$_3$(N$^R$,$^{R'}$-fmd), with R and R' independently being a C1-C5 hydrocarbon;
the Ti halide-containing precursor being TiBr$_3$(N$^{iPr}$-fmd);
the Ti halide-containing precursor being TiI$_3$(N$^{iPr}$-fmd);
the Ti halide-containing precursor being TiX$_3$(N$^{R, R'}$R''-amd), with R, R', and R'' independently being a C1-C5 hydrocarbon;
the Ti halide-containing precursor being TiBr$_3$(N$^{iPr}$Me-amd);
the Ti halide-containing precursor being TiI$_3$(N$^{iPr}$Me-amd);
the Ti halide-containing precursor being TiBr$_2$(—N(R)—C$_2$H$_4$—N(R)—) with each R independently being a C1-C5 hydrocarbon;
the Ti halide-containing precursor being TiIBr$_2$(—N(R)—C$_2$H$_4$—N(R)—) with each R independently being a C1-C5 hydrocarbon;
the Ti-containing film forming compositions comprising between approximately 0.1 molar % and approximately 50 molar % of the titanium halide-containing precursors;
the Ti-containing film forming composition having a viscosity between approximately 1 and approximately 50 cps;
the Ti-containing film forming composition having a viscosity, between approximately 1 and approximately 20 cps;
the Ti-containing film forming composition comprising between approximately 95% w/w to approximately 100% w/w of the titanium halide-containing precursors;
the Ti-containing film forming composition comprising between approximately 99% w/w to approximately 100% w/w of the titanium halide-containing precursors;
the Ti-containing film forming composition further comprising a solvent;
the Ti-containing film forming composition comprising between approximately 0% w/w and 10% w/w of a hydrocarbon solvent or of free adduct;
the Ti-containing film forming composition comprising between approximately 0% w/w and 5% w/w of a hydrocarbon solvent or of free adduct;
the Ti-containing film forming composition comprising between approximately 0% w/w and 5 ppm of H$_2$O;
the Ti-containing film forming composition comprising between approximately 0% w/w and 0.2% w/w of a mixture of oxybromide (TiBr$_2$(=O)), hydroxybromide (TiBr$_3$(OH)), and oxides (TiO$_2$);

the Ti-containing film forming composition comprising between approximately 0 w/w and 0.1% w/w of a mixture of oxybromide (TiBr$_2$(=O)), hydroxybromide (TiBr$_3$(OH)), and oxides (TiO$_2$);

the Ti-containing film forming composition comprising between approximately 0% w/w and 0.2% w/w of a mixture of oxyiodide (TiI$_2$(=O)), hydroxyiodide (TiI$_3$(OH)), and oxides (TiO$_2$);

the Ti-containing film forming composition comprising between approximately 0% w/w and 0.1% w/w of a mixture of oxyiodide (TiI$_2$(=O)), hydroxyiodide (TiI$_3$(OH)), and oxides (TiO$_2$);

the Ti-containing film forming composition comprising between approximately 0 w/w and 0.1% w/w of hydrogen bromide (HBr);

the Ti-containing film forming composition comprising between approximately 0 w/w and 0.1% w/w of hydrogen iodide (HI);

the Ti-containing film forming composition comprising between approximately 0% w/w and 0.2% w/w of TiX$_4$:SR'$_2$, wherein R$_4 \neq$R;

the solvent being selected from the group consisting of C1-C16 hydrocarbons, whether saturated or unsaturated, ketones, ethers, glymes, esters, tetrahydrofuran (THF), dimethyl oxalate (DMO), and combinations thereof;

the solvent being a C1-C16 hydrocarbon;

the solvent being a C1-C16 halogenated hydrocarbon;

the solvent being tetrahydrofuran (THF);

the solvent being DMO;

the solvent being an ether;

the solvent being a glyme; or the difference between the boiling point of the Ti halide-containing precursor and the solvent being less than 100° C.

Also disclosed are Ti-containing film forming compositions delivery devices comprising a canister having an inlet conduit and an outlet conduit and containing any of the Ti-containing film forming compositions disclosed above. The disclosed delivery devices may include one or more of the following aspects:

the Ti-containing film forming composition having a total concentration of metal contaminants of less than 10 ppmw;

an end of the inlet conduit located above a surface of the Ti-containing film forming composition and an end of the outlet conduit located above the surface of the Ti-containing film forming composition;

an end of the inlet conduit located above a surface of the Ti-containing film forming composition and an end of the outlet conduit located below the surface of the Ti-containing film forming composition;

an end of the inlet conduit located below a surface of the Ti-containing film forming composition and an end of the outlet conduit located above the surface of the Ti-containing film forming composition; or the titanium halide-containing precursor being TiBr$_4$:S(nPr)$_2$.

Also disclosed are processes for the deposition of Ti-containing films on one or more substrates. At least one Ti-containing film forming composition disclosed above is introduced into a reactor having at least one substrate disposed therein. At least part of the titanium halide-containing precursor is deposited onto the substrate(s) to form the Ti-containing film. The disclosed processes may further include one or more of the following aspects:

introducing at least one reactant into the reactor;

the reactant being plasma-treated;

the reactant being remote plasma-treated;

the reactant not being plasma-treated;

the reactant being selected from the group consisting of H$_2$, NH$_3$, hydrazines (such as N$_2$H$_4$, MeHNNH$_2$, MeHNNHMe), organic amines (such as NMeH$_2$, NEtH$_2$, NMe$_2$H, NEt$_2$H, NMe$_3$, NEt$_3$, cyclic amines like pyrrolidine or pyrimidine), nitriles (such as acetonitrile), diamines (such as ethylene diamine, dimethylethylene diamine, tetramethylethylene diamine), aminoalcohols (such as ethanolamine [HO—CH$_2$—CH$_2$—NH$_2$], bis ethanolamine [HN(C$_2$H$_5$OH)$_2$] or tris ethanolamine[N(C$_2$H$_5$OH)$_3$]), pyrazoline, and pyridine;

the reactant being selected from the group consisting of (SiH$_3$)$_3$N; N(SiH$_x$R$_{3-x}$)$_3$, with each x independently 1-3 and each R independently alkyl or NR'$_2$, with each R' independently H or C1-C4 alkyl (such as (H$_3$Si)$_2$N(SiH$_2$NEt$_2$), (H$_3$Si)$_2$N(SiH$_2$NiPr$_2$), or (H$_3$Si)$_2$N(SiH$_2$iPr)); R$_3$Si—NH—SiR$_3$, with each R independently H, Cl, Br, I, or a C1-C4 alkyl group (such as H$_3$Si—NH—SiH$_3$, H$_2$ISi—NH—SiH$_3$, or Me$_3$Si—NH—SiMe$_3$); hydridosilanes (such as SiH$_4$, Si$_2$H$_6$, Si$_3$H$_8$, Si$_4$H$_{10}$, Si$_5$H$_{10}$, Si$_6$H$_{12}$); chlorosilanes and chloropolysilanes (such as SiHCl$_3$, SiH$_2$Cl$_2$, SiH$_3$Cl, Si$_2$Cl$_6$, Si$_2$HCl$_5$, Si$_3$Cl$_8$); bromosilanes and bromopolysilanes (such as SiHBr$_3$, SiH$_2$Br$_2$, SiH$_3$Br, Si$_2$Br$_6$, Si$_2$HBr$_5$, Si$_3$Br$_8$); iodosilanes and iodopolysilanes (such as SiHI$_3$, SiH$_2$I$_2$, SiH$_3$I, Si$_2$I$_6$, Si$_2$HI$_5$, Si$_3$I$_8$); alkylsilanes (such as Me$_2$SiH$_2$, Et$_2$SiH$_2$, MeSiH$_3$, EtSiH$_3$); and am inosilanes (such as tris(dimethylamino)silane, bis(diethylamino)silane, di-isopropylaminosilane and other mono, bis or tris aminosilanes); radicals thereof; or mixtures thereof;

the reactant being selected from the group consisting of NH$_3$, N(SiH$_3$)$_3$, aminosilanes, and mixtures thereof;

the reactant being selected from trialkylaluminum, dialkylaluminum halide, alkylaluminum halide, alkylamino and alkoxy derivatives of aluminum, alanes, amine-adducted alanes, and mixtures thereof;

the reactant being NH$_3$;

the reactant being selected from the group consisting of: O$_2$, O$_3$, H$_2$O, H$_2$O$_2$, NO, N$_2$O, NO$_2$, an alcohol, a diol (such as ethylene glycol), plasma activated oxygen radicals thereof, and mixtures thereof;

the reactant being H$_2$O;

the reactant being O$_2$;

the reactant being plasma treated O$_2$;

the reactant being O$_3$;

the reactant being selected from the group consisting of NH$_3$, hydrazine and substituted hydrazines, amines such as primary amines (methylamine, ethylamine, isopropylamine, tertbutylamine), secondary amines (such as dimethylamine, diethylamine, ethylmethylamine, di-isopropylamine, pyrrolidine), or tertiary amines (such as triethylamine (TEA), trimethylamine (TMA));

the reactant being NH$_3$;

the reactant being hydrazine or substituted hydrazines;

the reactant being primary amines, such as methylamine, ethylamine, isopropylamine, tertbutylamine;

the reactant being secondary amines, such as dimethylamine, diethylamine, ethylmethylamine, bis-isopropylamine, pyrrolidine;

the reactant being tertiary amines, such as TEA, TMA;

the reactant being a Si-containing precursor;
the Si-containing precursor being selected from the group consisting of $SiH_4$, $Si_2H_6$, $Si_4H_8$, trisilylamine (TSA), and substituted TSA (substituted by alkyl, dialkylamine, halide);
the Si-containing precursor being TSA;
the Ti-containing film forming composition and the reactant being introduced into the reactor simultaneously;
the reactor being configured for chemical vapor deposition;
the reactor being configured for plasma enhanced chemical vapor deposition;
the Ti-containing film forming composition and the reactant being introduced into the chamber sequentially;
the reactor being configured for atomic layer deposition;
the reactor being configured for plasma enhanced atomic layer deposition;
the reactor being configured for spatial atomic layer deposition;
liberating the adduct A from the Ti halide-containing precursor;
the liberated adduct A forming a blocking agent;
introducing a blocking agent into the reactor;
the blocking agent being a self-assembling monolayer;
the blocking agent being an inhibitor;
the Ti-containing film being a titanium oxide ($Ti_nO_m$, wherein each n and m is an integer which inclusively range from 1 to 6);
the Ti-containing film being $TiO_2$;
the Ti-containing film being TiN;
the Ti-containing film being TiSiN;
the Ti-containing film being $TiM_iO_x$, wherein i ranges from 0 to 1; x ranges from 1 to 6; and M is any element from the Periodic table;
the Ti-containing film being $TiM_iO_x$, wherein i ranges from 0 to 1; x ranges from 1 to 6; and M is Si, Al, or Ge;
the Ti-containing film being $TiM_iN_y$, wherein i ranges from 0 to 1; y ranges from 0.5 to 6; and M is any element from the Periodic table;
the Ti-containing film being $TiM_iN_y$, wherein i ranges from 0 to 1; y ranges from 0.5 to 6; and M is Si, Al, or Ge;
the Ti-containing film being TiCN;
the Ti-containing film being TiAl;
the Ti-containing film being TiAlN;
the Ti-containing film being $TiM_iN_yO_x$, wherein i ranges from 0 to 1; x and y range from 1 to 6; and M is any element from the Periodic table;
the Ti-containing film being $TiM_iN_yO_x$, wherein i ranges from 0 to 1; x and y range from 1 to 6; and M is Si, Al, or Ge;
the Ti-containing film having a C concentration ranging from approximately 0 at % to 5 at %;
the Ti-containing film having a O concentration ranging from approximately 0 at % to 40 at %;
the Ti-containing film having a S concentration ranging from approximately 0 at % to 2 at %;
the Ti-containing film having a Se concentration ranging from approximately 0 at % to 2 at %;
the Ti-containing film having a Te concentration ranging from approximately 0 at % to 2 at %;
the Ti-containing film having a P concentration ranging from approximately 0 at % to 2 at %;
the TiN-containing film forming an electrode in a capacitor structure;
the TiN-containing film forming a metal gate in a CMOS transistor or Flash memory;
the TiN-containing film forming a buried word line;
the Ti-containing film being a titanium silicide contact layer between conductive metal plugs and the underlying doped silicon layer in a CMOS transistor or Flash memory;
the Ti-containing film being selectively deposited onto a doped silicon layer but not a conductive metal plug; or
the Ti-containing film being a titanium nitride layer selectively deposited on a tungsten layer to form a buried word line.

Notation and Nomenclature

Certain abbreviations, symbols, and terms are used throughout the following description and claims, and include:

As used herein, the indefinite article "a" or "an" means one or more.

As used herein, the terms "approximately" or "about" mean ±10% of the value stated.

As used herein, the term "independently" when used in the context of describing R groups should be understood to denote that the subject R group is not only independently selected relative to other R groups bearing the same or different subscripts or superscripts, but is also independently selected relative to any additional species of that same R group. For example in the formula $MR^1_x(NR^2R^3)_{(4-x)}$, where x is 2 or 3, the two or three $R^1$ groups may, but need not be identical to each other or to $R^2$ or to $R^3$. Further, it should be understood that unless specifically stated otherwise, values of R groups are independent of each other when used in different formulas.

As used herein, the term "adduct" means a molecular entity which is formed by direct combination of two separate molecule entities in such a way there is connectivity but no loss of atoms; the term "Lewis acid" means a molecular entity that is an electron-pair acceptor; the term "Lewis base" means a molecular entity able to provide a pair of electrons and thus coordinate to a Lewis acid; and the term "Lewis adduct" means an adduct formed between a Lewis acid and a Lewis base.

As used herein, the term "hydrocarbyl group" refers to a functional group containing carbon and hydrogen; the term "alkyl group" refers to saturated functional groups containing exclusively carbon and hydrogen atoms. The hydrocarbyl group may be saturated or unsaturated. Either term refers to linear, branched, or cyclic groups. Examples of linear alkyl groups include without limitation, methyl groups, ethyl groups, propyl groups, butyl groups, etc. Examples of branched alkyls groups include without limitation, t-butyl. Examples of cyclic alkyl groups include without limitation, cyclopropyl groups, cyclopentyl groups, cyclohexyl groups, etc.

As used herein, the abbreviation "Me" refers to a methyl group; the abbreviation "Et" refers to an ethyl group; the abbreviation "Pr" refers to a propyl group; the abbreviation "nPr" refers to a "normal" or linear propyl group; the abbreviation "iPr" refers to an isopropyl group; the abbreviation "Bu" refers to a butyl group; the abbreviation "nBu" refers to a "normal" or linear butyl group; the abbreviation "tBu" refers to a tert-butyl group, also known as 1,1-dimethylethyl; the abbreviation "sBu" refers to a sec-butyl group, also known as 1-methylpropyl; the abbreviation "iBu" refers to an iso-butyl group, also known as 2-methylpropyl; the term "amyl" refers to an amyl or pentyl group (i.e., a C5 alkyl group); the term "tAmyl" refers to a tert-amyl group, also known as 1,1-dimethylpropyl; the term "halide" refers to the halogen anions F⁻, Cl⁻, Br⁻, and I⁻; and the abbreviation "TMS" refers to trimethylsilyl or —SiMe₃.

As used herein, the abbreviation "$N^{R,\ R'}R''$-amd" or $N^R$ R"-amd when R=R' refers to the amidinate ligand [R—N—C(R")=N—R'], wherein R, R' and R" are defined alkyl groups, such as Me, Et, nPr, iPr, nBu, iBi, sBu or tBu; the abbreviation "$N^{R,\ R'}$-fmd" or $N^R$-fmd when R=R' refers to the formidinate ligand [R—N—C(H)=N—R'], wherein R and R' are defined alkyl groups, such as Me, Et, nPr, iPr, nBu, iBi, sBu or tBu; the abbreviation "$N^{R,\ R'},N^{R'',\ R'''}$-gnd" or $N^R$, $N^{R''}$-gnd when R=R' and R"=R''' refers to the guanidinate ligand [R—N—C(NR"R''')=NR'], wherein R, R', R" and R''' are defined alkyl group such as Me, Et, nPr, iPr, nBu, iBi, sBu or tBu. Although depicted here as having a double bond between the C and N of the ligand backbone, one of ordinary skill in the art will recognize that the amidinate, formidinate and guanidinate ligands do not contain a fixed double bond. Instead, one electron is delocalized amongst the N—C—N chain.

i) 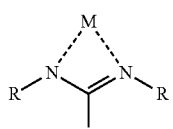

Amidinate ligand ii) 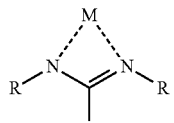

Formamidinate ligand iii) 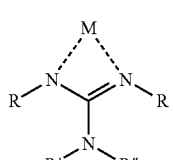

Guanidinate ligand

The standard abbreviations of the elements from the periodic table of elements are used herein. It should be understood that elements may be referred to by these abbreviations (e.g., Ti refers to titanium, Br refers to bromine, C refers to carbon, etc.). Additionally, Group 3 refers to Group 3 of the Periodic Table (i.e., Sc, Y, La, or Ac) and Group 5 refers to Group 5 of the Periodic Table (i.e., V, Nb, or Ta).

Any and all ranges recited herein are inclusive of their endpoints (i.e., x=1 to 4 or x ranges from 1 to 4 includes x=1, x=4, and x=any number in between), irrespective of whether the term "inclusively" is used.

As used herein, the term "selective" or "selectively" means to deposit a film on one type of substrate while not depositing a film on a second type of substrate or to preferentially grow a film faster on one type of substrate than on a second type of substrate. For example, the substrate may contain a tungsten plug or channel surrounded by a doped silicon dioxide. The disclosed Ti-containing film forming composition may deposit a Ti-containing film on the tungsten, but not on the surrounding silicon dioxide, or vice versa. Alternatively, during the same exposure period, the disclosed Ti-containing film forming composition may form a thicker film on one type of substrate than on another type of substrate. The thicker film may be due to a faster growth rate or shorter induction time. As a result, the disclosed Ti-containing film forming compositions selectively deposit a Ti-containing film on one substrate as compared to a second substrate.

Please note that the films or layers deposited, such as titanium oxide or titanium nitride, may be listed throughout the specification and claims without reference to their proper stoichiometry (i.e., $TiO_2$, $Ti_3N_4$). The layers may include but are not limited to pure (Ti) layers, carbide ($Ti_oC_p$) layers, nitride ($Ti_kN_l$) layers, oxide ($Ti_nO_m$) layers, or mixtures thereof, wherein k, l, m, n, o, and p inclusively range from 1 to 6. For instance, titanium oxide is $Ti_nO_m$, wherein n ranges from 0.5 to 1.5 and m ranges from 1.5 to 3.5. More preferably, the titanium oxide layer is $TiO_2$. These films may also contain Hydrogen, typically from 0 at % to 15 at %. However, since not routinely measured, any film compositions given ignore their H content, unless explicitly stated otherwise.

BRIEF DESCRIPTION OF THE FIGURES

For a further understanding of the nature and objects of the present invention, reference should be made to the following detailed description, taken in conjunction with the accompanying figures wherein.

DESCRIPTION OF PREFERRED EMBODIMENTS

Figure 1:
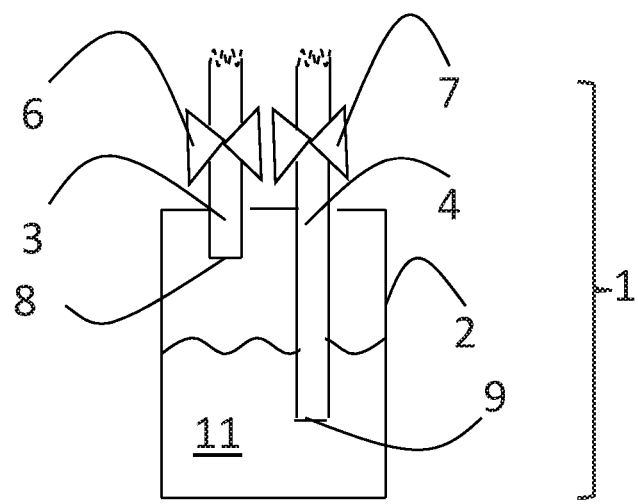
FIG. 1 is a side view of one embodiment of a liquid Ti-containing film forming composition delivery device 1.

Ti-containing film forming compositions are disclosed. The Ti-containing film forming compositions comprise Ti halide-containing precursors having one of the following formula:

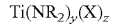

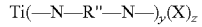

with b=3 when c=3; b=4 when c=1 or 2; y=1-3; z=1-3; y+z=4; X=Br or I; A=$SR_2$, $SeR_2$, $TeR_2$, or $PR_3$; each R is independently H, a C1-C5 hydrocarbon, or $SiR'_3$, with each R' independently being H or a C1-C5 hydrocarbon; and R''=C1-C5 hydrocarbon. Preferably, b=4 and c=1 or 2. However, in certain embodiments, the octahedral $TiX_3:A_3$ is the most stable embodiment.

Exemplary Ti halide-containing precursors having the formula $TiX_4:A_c$, with c=1 or 2 and X=Br or I; include $TiX_4:SR_2$, $TiX_4:(SR_2)_2$, $TiX_4:SeR_2$, $TiX_4:(SeR_2)_2$, $TiX_4:TeR_2$, or $TiX_4:(TeR_2)_2$, with each R independently a C1-C5 hydrocarbon. The two R groups may also be linked to form a cyclic structure. When c=2, each R is preferably a smaller hydrocarbon ligand due to steric hindrance. For example, when c=2, each R may independently be a C1-2 hydrocarbon. In contrast, when c=1, the precursor enjoys less steric hindrance and each R may independently be a C3-C5 hydrocarbon.

When X=Br and A=$SR_2$, exemplary $TiX_4:A_c$ precursors include $TiBr_4:SEt_2$, $TiBr_4:SPr_2$, $TiBr_4:S(nPr)_2$, $TiBr_4:S(iPr)_2$, $TiBr_4:SBu_2$, $TiBr_4:S(nBu)_2$, $TiBr_4:S(tBu)_2$, $TiBr_4:S(iBu)_2$, $TiBr_4:S(sBu)_2$, $TiBr_4:(SMe_2)_2$, $TiBr_4:(SEt_2)_2$, $TiBr_4:(SMeEt)_2$, or $TiBr_4:(tetrahydrothiophene)_2$.

When X=I and A=$SR_2$, exemplary $TiX_4:A_c$ precursors include $TiI_4:SEt_2$, $TiI_4:S(nPr)_2$, $TiI_4:S(iPr)_2$, $TiI_4:SBu_2$, $TiI_4:S(nBu)_2$, $TiI_4:S(tBu)_2$, $TiI_4:S(iBu)_2$, $TiI_4:S(sBu)_2$, $TiI_4:(SEt_2)_2$, $TiI_4:(SMe_2)_2$, $TiI_4:(SMeEt)_2$, or $TiI_4:(tetrahydrothiophene)_2$.

Exemplary $TiX_4:(SeR_2)_c$ precursors include $TiBr_4:SePr_2$, $TiBr_4:SeBu_2$, $TiBr_4:(SeMe_2)_2$, $TiBr_4:(SeEt_2)_2$, $TiBr_4:(SeMeEt)_2$, or $TiBr_4:(tetrahydroselenophene)_2$.

Exemplary $TiX_4:(TeR_2)_c$ precursors include $TiBr_4:TePr_2$, $TiBr_4:TeBu_2$, $TiBr_4:(TeMe_2)_2$, $TiBr_4:(TeEt_2)_2$, $TiBr_4:(TeMeEt)_2$, or $TiBr_4:(tetrahydrotellurophene)_2$.

These precursors may be prepared by direct reaction of the Ti halide with an excess of the ligand in any solvent. See, e.g., Fowles et al., Journal of the less common metals, 8, 1965, pp. 47-50. The halide starting material is commercially available. The $SR_2$, $SeR_2$, and $TeR_2$ starting material may be commercially available and/or synthesized by methods known in the literature. An exemplary synthesis method containing further details is provided in the Examples that follow.

Exemplary Ti halide-containing precursors having the formula $TiX_b:A_c$, with b=3 or 4, c=1-3, and X=Br or I; include $TiX_b:(PR_3)_c$ with each R independently H or a C1-C5 hydrocarbon. Adjacent R groups may also be linked to form a cyclic structure. When c=2, each R is preferably a smaller hydrocarbon ligand due to steric hindrance. For example, when c=2, each R may independently be H or a C1-2 hydrocarbon. In contrast, when c=1, the precursor enjoys less steric hindrance and each R may independently be a C3-C10 hydrocarbon. Exemplary $TiX_b:(PR_3)_c$ precursors include $TiBr_4:PH_3$, $TiBr_4:(PH_3)_2$, or $TiBr_3:(PH_3)_3$.

These precursors may be prepared by direct reaction of the Ti halide with an excess of the $PR_3$. See, e.g., R. Höltje, Zeitschrift fuer Anorganische and Allgemeine Chemie, 1930, 190, pp 241-256.

Another exemplary Ti halide-containing precursor has the formula $TiX_4:(R_2P—(CH_2)_n—PR_2)$ or $TiX_3:(R_2P—(CH_2)_n—PR_2)$, with each R independently a C1-5 hydrocarbon and n=1-4. These precursors may be synthesized by direct reaction of the Ti halide with an excess of the $R_2P—CH_2—PR_2$. See, e.g., Fowles et al., Journal of the less common metals, 8, 1965, pp. 47-50. One of ordinary skill in the art will recognize that the $R_2P—CH_2—PR_2$ ligand may reduce Ti(IV) to Ti(III). As a result, the Ti-containing film forming compositions may include a combination of both of the $TiX_4:(R_2P—(CH_2)_n—PR_2)$ and $TiX_3:(R_2P—(CH_2)_n—PR_2)$ precursors.

When X=Br, exemplary $TiX_4:(R_2P—(CH_2)_n—PR_2)$ precursors include $TiBr_4:(Me_2P—(CH_2)_n—PMe_2)$, $TiBr_4:(EtMeP—(CH_2)_n—PMeEt)$, $TiBr_4:(Et_2P—(CH_2)_n—PEt_2)$, $TiBr_4:(iPr_2P—(CH_2)_n—PiPr_2)$, $TiBr_4:(HiPrP—(CH_2)_n—PHiPr)$, $TiBr_4:(tBu_2P—(CH_2)_n—PtBu_2)$, $TiBr_4:(tBuHP—(CH_2)_n—PHtBu)$, $TiBr_4:(tAmHP—(CH_2)_n—PHtAm)$, $TiBr_4:(Me_2P—(CH_2)—PMe_2)$, $TiBr_4:(EtMeP—(CH_2)—PMeEt)$, $TiBr_4:(Et_2P—(CH_2)—PEt_2)$, $TiBr_4:(iPr_2P—(CH_2)—PiPr_2)$, $TiBr_4:(HiPrP—(CH_2)—PHiPr)$, $TiBr_4:(tBu_2P—(CH_2)—PtBu_2)$, $TiBr_4:(tBuHP—(CH_2)—PHtBu)$, $TiBr_4:(tAmHP—(CH_2)—PHtAm)$, $TiBr_4:(Me_2P—(CH_2)_2—PMe_2)$, $TiBr_4:(EtMeP—(CH_2)_2—PMeEt)$, $TiBr_4:(Et_2P—(CH_2)_2—PEt_2)$, $TiBr_4:(iPr_2P—(CH_2)_2—PiPr_2)$, $TiBr_4:(HiPrP—(CH_2)_2—PHiPr)$, $TiBr_4:(tBu_2P—(CH_2)_2—PtBu_2)$, $TiBr_4:(tBuHP—(CH_2)_2—PHtBu)$, or $TiBr_4:(tAmHP—(CH_2)_2—PHtAm)$.

Exemplary $TiX_3:(R_2P—(CH_2)_n—PR_2)$ precursors include $TiBr_3:(Me_2P—(CH_2)_n—PMe_2)$, $TiBr_3:(EtMeP—(CH_2)_n—PMeEt)$, $TiBr_3:(Et_2P—(CH_2)_n—PEt_2)$, $TiBr_3:(iPr_2P—(CH_2)_n—PiPr_2)$, $TiBr_3:(HiPrP—(CH_2)_n—PHiPr)$, $TiBr_3:(tBu_2P—(CH_2)_n—PtBu_2)$, $TiBr_3:(tBuHP—(CH_2)_n—PHtBu)$, $TiBr_3:(tAmHP—(CH_2)_n—PHtAm)$, $TiBr_3:(Me_2P—(CH_2)—PMe_2)$, $TiBr_3:(EtMeP—(CH_2)—PMeEt)$, $TiBr_3:(Et_2P—(CH_2)—PEt_2)$, $TiBr_3:(iPr_2P—(CH_2)—PiPr_2)$, $TiBr_3:(HiPrP—(CH_2)—PHiPr)$, $TiBr_3:(tBu_2P—(CH_2)—PtBu_2)$, $TiBr_3:(tBuHP—(CH_2)—PHtBu)$, $TiBr_3:(tAmHP—(CH_2)—PHtAm)$, $TiBr_3:(Me_2P—(CH_2)_2—PMe_2)$, $TiBr_3:(EtMeP—(CH_2)_2—PMeEt)$, $TiBr_3:(Et_2P—(CH_2)_2—PEt_2)$, $TiBr_3:(iPr_2P—(CH_2)_2—PiPr_2)$, $TiBr_3:(HiPrP—(CH_2)_2—PHiPr)$, $TiBr_3:(tBu_2P—(CH_2)_2—PtBu_2)$, $TiBr_3:(tBuHP—(CH_2)_2—PHtBu)$, or $TiBr_3:(tAmHP—(CH_2)_2—PHtAm)$.

When X=I, exemplary $TiX_4:(R_2P—(CH_2)_n—PR_2)$ precursors include $TiI_4:(Me_2P—(CH_2)_n—PMe_2)$, $TiI_4:(EtMeP—(CH_2)_n—PMeEt)$, $TiI_4:(Et_2P—(CH_2)_n—PEt_2)$, $TiI_4:(iPr_2P—(CH_2)_n—PiPr_2)$, $TiI_4:(HiPrP—(CH_2)_n—PHiPr)$, $TiI_4:(tBu_2P—(CH_2)_n—PtBu_2)$, $TiI_4:(tBuHP—(CH_2)_n—PHtBu)$, $TiI_4:(tAmHP—(CH_2)_n—PHtAm)$, $TiI_4:(Me_2P—(CH_2)—PMe_2)$, $TiI_4:(EtMeP—(CH_2)—PMeEt)$, $TiI_4:(Et_2P—(CH_2)—PEt_2)$, $TiI_4:(iPr_2P—(CH_2)—PiPr_2)$, $TiI_4:(HiPrP—(CH_2)—PHiPr)$, $TiI_4:(tBu_2P—(CH_2)—PtBu_2)$, $TiI_4:(tBuHP—(CH_2)—PHtBu)$, $TiI_4:(tAmHP—(CH_2)—PHtAm)$, $TiI_4:(Me_2P—(CH_2)_2—PMe_2)$, $TiI_4:(EtMeP—(CH_2)_2—PMeEt)$, $TiI_4:(Et_2P—(CH_2)_2—PEt_2)$, $TiI_4:(iPr_2P—(CH_2)_2—PiPr_2)$, $TiI_4:(HiPrP—(CH_2)_2—PHiPr)$, $TiI_4:(tBu_2P—(CH_2)_2—PtBu_2)$, $TiI_4:(tBuHP—(CH_2)_2—PHtBu)$, or $TiI_4:(tAmHP—(CH_2)_2—PHtAm)$.

Exemplary $TiX_3:(R_2P—(CH_2)_n—PR_2)$ precursors include $TiI_3:(Me_2P—(CH_2)_n—PMe_2)$, $TiI_3:(EtMeP—(CH_2)_n—PMeEt)$, $TiI_3:(Et_2P—(CH_2)_n—PEt_2)$, $TiI_3:(iPr_2P—(CH_2)_n—PiPr_2)$, $TiI_3:(HiPrP—(CH_2)_n—PHiPr)$, $TiI_3:(tBu_2P—(CH_2)_n—PtBu_2)$, $TiI_3:(tBuHP—(CH_2)_n—

PHtBu), TiI$_3$:(tAmHP—CH$_2$)$_n$—PHtAm), TiI$_3$:(Me$_2$P—(CH$_2$)—PMe$_2$), TiI$_3$:(EtMeP—(CH$_2$)—PMeEt), TiI$_3$:(Et$_2$P—(CH$_2$)—PEt$_2$), TiI$_3$:(iPr$_2$P—(CH$_2$)—PiPr$_2$), TiI$_3$:(HiPrP—(CH$_2$)—PHiPr), TiI$_3$:(tBu$_2$P—(CH$_2$)—PtBu$_2$), TiI$_3$:(tBuHP—(CH$_2$)—PHtBu), TiI$_3$:(tAmHP—(CH$_2$)—PHtAm), TiI$_3$:(Me$_2$P—(CH$_2$)$_2$—PMe$_2$), TiI$_3$:(EtMeP—(CH$_2$)$_2$—PMeEt), TiI$_3$:(Et$_2$P—(CH$_2$)$_2$—PEt$_2$), TiI$_3$:(iPr$_2$P—(CH$_2$)$_2$—PiPr$_2$), TiI$_3$:(HiPrP—(CH$_2$)$_2$—PHiPr), TiI$_3$:(tBu$_2$P—(CH$_2$)$_2$—PtBu$_2$), TiI$_3$:(tBuHP—(CH$_2$)$_2$—PHtBu), or TiI$_3$:(tAmHP—(CH$_2$)$_2$—PHtAm).

Exemplary Ti halide-containing precursors having the formula TiX$_4$:A$_c$, with c=1 and X=Br or I; include TiX$_4$:(R(=O)Cl), with R being a C2-C6 hydrocarbon. Exemplary TiX$_4$:(R(=O)Cl) precursors include TiBr$_4$:(Me-C(=O)Cl), TiBr$_4$:(Ph-C(=O)Cl), or TiI$_4$:(Me-C(=O)Cl). These precursors may be prepared by direct reaction of the Ti halide with an excess of the ligand without solvent or in CCl$_4$, benzene, toluene. See e.g. Eméleus et al., Complexes of Titanium and Zirconium Halides with Organic Ligands, J. Chemical Society (Resumed), 1958, pp. 4245-50.

Exemplary Ti halide-containing precursors having the formula TiX$_4$:A$_c$, with c=1 and X=Br or I; include TiX$_4$:(RNO$_2$), with R being a C1-C10 hydrocarbon. Exemplary TiX$_4$:(RNO$_2$) precursors include TiBr$_4$:(MeNO$_2$), TiI$_4$:(MeNO$_2$), TiBr$_4$:(EtNO$_2$), TiBr$_4$:(PrNO$_2$), or TiBr$_4$:(PhNO$_2$). These precursors may be prepared by direct reaction of the Ti halide with an excess of the ligand without solvent or in CCl$_4$, benzene, toluene. See e.g. Eméleus et al., Complexes of Titanium and Zirconium Halides with Organic Ligands, J. Chemical Society (Resumed), 1958, pp. 4245-50.

Exemplary Ti halide-containing precursors having the formula TiX$_4$:A$_c$, with c=2 and X=Br or I; include TiX$_4$:(R≡N)$_2$, with R being a C2-C10 hydrocarbon. Exemplary TiX$_4$:(R≡N)$_c$ precursors include TiBr$_4$:(Me-C≡N)$_2$, TiBr$_4$:(Et-C≡N)$_2$, TiBr$_4$:(Pr—C≡N)$_2$, TiBr$_4$:(Bu-C≡N)$_2$, or TiBr$_4$:(Ph-C≡N)$_2$. These precursors may be prepared by direct reaction of the Ti halide with an excess of the ligand without solvent or in CCl$_4$, benzene, toluene. See e.g. Eméleus et al., Complexes of Titanium and Zirconium Halides with Organic Ligands, J. Chemical Society (Resumed), 1958, pp. 4245-50.

Exemplary Ti halide-containing precursors having the formula TiX$_4$:A$_c$, with c=1 or 2 and X=Br or I; include TiX$_4$:(pyridine)$_c$. Exemplary TiX$_4$:(pyridine)$_c$ precursors include TiBr$_4$:pyridine. These precursors may be prepared by direct reaction of the Ti halide with an excess of the ligand without solvent or in CCl$_4$, benzene, toluene. See e.g. Eméleus et al., Complexes of Titanium and Zirconium Halides with Organic Ligands, J. Chemical Society (Resumed), 1958, pp. 4245-50.

Exemplary Ti halide-containing precursors having the formula TiX$_4$:A$_c$, with c=1 or 2 and X=Br or I; include TiX$_4$:(piperidine)$_c$. Exemplary TiX$_4$:(piperidine)$_c$ precursors include TiBr$_4$:piperidine or TiBr$_4$:2,2,6,6-tetramethylpiperidine. These precursors may be synthesized by direct reaction of the Ti halide with an excess of the ligand in benzene or toluene. See e.g. Dermer et al. in Zeitschrift fuer Anorganishce and Allgemeine Chemie (1934) 221 pp. 83-96.

Exemplary Ti halide-containing precursors having the formula Ti(NR$_2$)$_y$(X)$_z$, with y=1-3, z=1-3, y+z=4, X=Br or I, and each R independently H, a C1-C10 hydrocarbon, or SiR'$_3$, with each R' independently being H or a C1-C10 hydrocarbon include TiX$_3$(NR$_2$), TiX$_2$(NR$_2$)$_2$, or TiX(NR$_2$)$_3$. The two R groups may be linked to form a cyclic structure.

Exemplary TiX$_3$(NR$_2$) precursors include TiBr$_3$(NR$_2$) and TiI$_3$(NR$_2$), such as TiBr$_3$(NEt$_2$), TiBr$_3$(pyrrolidine), TiBr$_3$(pyridine), or TiBr$_3$(piperidine). These precursors may be synthesized by reaction of TiX$_4$ with Me$_3$Si(NR$_2$) as described by Buerger et al., Zeitschrift fuer Anorganische und Allgemeine Chemie, 370 (5-6), 1969, pp. 275-282.

Exemplary TiX$_2$(NR$_2$)$_2$ precursors include TiBr$_2$(NR$_2$)$_2$ and TiI$_2$(NR$_2$)$_2$, such as TiBr$_2$(NMe$_2$)$_2$. These precursors may be synthesized by metathesis of TiX$_4$ with Ti(NR$_2$)$_4$ as described by Buerger et al., Zeitschrift fuer Anorganische und Allgemeine CHemie, 370 (5-6), 1969, pp. 275-282.

Exemplary TiX(NR$_2$)$_3$ precursors include TiBr(NR$_2$)$_3$ and TiI(NR$_2$)$_3$. These precursors may be synthesized by reaction of TiX$_4$ with Ti(NR$_2$)$_4$ as described by Buerger et al., Zeitschrift fuer Anorganische und Allgemeine CHemie, 370 (5-6), 1969, pp. 275-282.

Exemplary Ti halide-containing precursors having the formula Ti(—N—R"—N—)$_y$(X)$_z$, with y=1-3, z=1-3, y+z=4, X=Br or I, and R" a C1-C10 hydrocarbon, include TiBr$_3$(N$^{iPr}$-fmd), TiBr$_3$(N$^{iPr}$ Me-amd), or TiBr$_2$(—N(R)—C$_2$H$_4$—N(R)—)$_2$. These precursors may be synthesized by reaction of TiBr$_4$ or TiI$_4$ and trimethylsilyl derivative of amidinate ligand (e.g. TiBr$_4$ and TMS-N$^{iPr}$ Me-amd). Exemplary synthesis methods are described for titanium chloride complexes in D. Fenske et al. Z. Naturforsch. 43b, 1611-1615 (1988); D. Liguori et al., Macromolecules 2003, 36, 5451-5458.

One of ordinary skill in the art will recognize the sources for the equipment used to practice the disclosed synthesis methods. Some level of customization of the components may be required based upon the desired temperature range, pressure range, local regulations, etc. Exemplary equipment suppliers include Buchi Glass Uster AG, Shandong Chem-Sta Machinery Manufacturing Co. Ltd., Jiangsu Shajiabang Chemical Equipment Co. Ltd, etc.

To ensure process reliability, the Ti-containing film forming compositions may be purified by continuous or fractional batch distillation or sublimation prior to use to a purity ranging from approximately 93% w/w to approximately 100% w/w, preferably ranging from approximately 99% w/w to approximately 100% w/w. The Ti-containing film forming compositions may contain any of the following impurities: undesired congeneric species; excess adduct; hydrogen halides (HX); solvents; halogenated metal compounds (TiX); or other reaction products. In one alternative, the total quantity of these impurities is below 0.1% w/w.

High purity product may be obtained by using high purity reactants. For example, the SR$_2$ adduct may contain traces of SR'$_2$, wherein R≠R. Preferably, the Ti-containing film forming composition comprises between approximately 0% w/w and 0.2% w/w of TiX$_b$:(SR'2)$_c$, wherein R'≠R. The SR'$_2$ levels may be analyzed in either the starting material or finished product using GC and/or NMR.

The Ti-containing film forming compositions should contain no water because the molecules will hydrolyze (e.g., between approximately 0% w/w and 5 ppm of H$_2$O). Any water present in the Ti-containing film forming compositions may result in formation of undesired oxyhalides (TiBr$_2$(=O) or TiI$_2$(=O)), hydroxyhalides (TiBr$_3$(OH) or TiI$_3$(OH)), and oxides (TiO$_2$). The total amount of the combination of these three impurities in the Ti-containing film forming composition should be less than 0.2% w/w, and preferably less than 0.1% w/w. These impurities may be detected using NMR, FTIR, TGA, or combinations thereof.

The amount of hydrogen halide (i.e., HBr or HI) reaction by-product should also be minimized because it may react with components in the delivery lines and deposition chamber. HX may also be detrimental to the underlying substrate. The Ti-containing film forming compositions should contain less than 0.1% w/w and preferably less than 0.01% w/w of any HX by-products. These impurities may be detected using FTIR and/or GC.

The concentration of each of hexane, pentane, dimethyl ether, or anisole in the purified Ti-containing film forming compositions may range from approximately 0% w/w to approximately 5% w/w, preferably from approximately 0% w/w to approximately 0.1% w/w. Solvents may be used in the composition's synthesis. Separation of the solvents from the precursor may be difficult if both have similar boiling points. Cooling the mixture may produce solid precursor in liquid solvent, which may be separated by filtration. Vacuum distillation may also be used, provided the precursor reaction product is not heated above approximately its decomposition point.

In one alternative, the disclosed Ti-containing film forming compositions contain less than 5% v/v, preferably less than 1% v/v, more preferably less than 0.1% v/v, and even more preferably less than 0.01% v/v of any of its undesired congeneric species, reactants, or other reaction products. This alternative may provide better process repeatability. This alternative may be produced by distillation of the Ti-containing precursors.

In another alternative, the disclosed Ti-containing film forming compositions may contain between 5% v/v and 50% v/v of one or more cogeneric Ti halide-containing precursors, reactants, or other reaction products, particularly when the mixture provides improved process parameters or isolation of the target compound is too difficult or expensive. For example, a mixture of two Ti halide-containing precursors, such as $TiBr_4$:($iPr_2$P—($CH_2$)—$PiPr_2$) and $TiBr_3$:($iPr_2$P—($CH_2$)—$PiPr_2$), may produce a stable, liquid mixture suitable for vapor deposition.

The concentration of trace metals and metalloids in the purified Ti-containing film forming compositions may each range from approximately 0 ppm to approximately 5 ppm, preferably from approximately 0 ppm to approximately 1 ppm, and more preferably from approximately 0 ppb to approximately 500 ppb. These metal impurities include, but are not limited to, Aluminum (Al), Silver (Ag), Arsenic (As), Barium (Ba), Beryllium (Be), Bismuth (Bi), Cadmium (Cd), Calcium (Ca), Chromium (Cr), Cobalt (Co), Copper (Cu), Gallium (Ga), Germanium (Ge), Hafnium (Hf), Indium (In), Iron (Fe), Lead (Pb), Lithium (Li), Magnesium (Mg), Manganese (Mn), Tungsten (W), Nickel (Ni), Potassium (K), Sodium (Na), Strontium (Sr), Thorium (Th), Tin (Sn), Uranium (U), Vanadium (V), Zinc (Zn), and Zirconium (Zr).

The benefit of the disclosed precursors is a reduced melting point when compared to their $TiX_4$ analogs. For titanium iodide-containing precursors, the Ti halide-containing precursor may have a melting point between approximately −50° C. and approximately 150° C. at standard temperature and pressure, preferably between approximately −50° C. and approximately 30° C. at standard temperature pressure. For titanium bromide-containing precursors, the Ti halide-containing precursor may have a melting point between approximately −50° C. and approximately 39° C. at standard temperature and pressure. Preferably, the Ti halide-containing precursor is a liquid at standard temperature and pressure because the reproducible and stable production of vapor from solid precursors is challenging at best. Solid precursors may be dissolved in a solvent and the solution vaporized, but that may introduce impermissible contamination issues from the solvent into the resulting film. Alternatively, a sublimator may be used to produce vapors from solid materials directly, but the grain size, solid distribution in the sublimator, and vapor pressure of the solid itself make it very difficult to provide a consistent and reproducible concentration of the vapor to the semiconductor process.

Applicants also expect that the Ti-adduct bonds will break at the deposition temperature. As a result, no film contamination is expected from inclusion of the adduct in the Ti halide-containing precursor. As such, these precursors should behave as $TiBr_4$ and $TiI_4$, but be easier to handle and use owing to their lower melting point. The disclosed Ti halide-containing precursor are also better than $TiCl_4$ due to a lower deposition temperature and the absence of highly corrosive Cl.

Finally, Applicants believe that the disclosed Ti-containing film forming compositions may be more stable and less hydrolysable than the analogous chloride containing compositions. The disclosed Ti-containing film forming compositions may also exhibit less etching damage to the substrate and reactor than the analogous chloride containing compositions. Testing was performed using the $TiBr_4$—$S(nPr)_2$ molecules and no substrate damage was evident on $Al_2O_3$, $HfO_2$, $Nb_2O_5$, $SiO_2$, or $ZrO_2$ films at 300° C., 350° C., 400° C., or 450° C. This is somewhat surprising because HBr is more acidic than HCl (pKa HCl=−7, pKa HBr=−9, and pKa HI=−10).

The Ti-containing film forming compositions may exhibit (i) sufficient volatility to provide a rapid and reproducible delivery into the reaction chamber from the vessel in which they are stored, (ii) high thermal stability to avoid decomposition during the storage in the canister and to enable self-limiting growth in ALD mode at high temperature, typically >150° C. for dielectric films and >275° C. for conductive films, (iii) appropriate reactivity toward the substrate terminal functions and with the reacting gas to an easy conversion into the desired film, and (iv) high purity to obtain a film with low impurities.

Also disclosed are methods for forming Ti-containing layers on a substrate using a vapor deposition process. The method may be useful in the manufacture of semiconductor, photovoltaic, LCD-TFT, or flat panel type devices. The disclosed Ti-containing film forming compositions may be used to deposit thin Ti-containing films using any deposition methods known to those of skill in the art. Examples of suitable vapor deposition methods include chemical vapor deposition (CVD) or atomic layer deposition (ALD). Exemplary CVD methods include thermal CVD, plasma enhanced CVD (PECVD), pulsed CVD (PCVD), low pressure CVD (LPCVD), sub-atmospheric CVD (SACVD) or atmospheric pressure CVD (APCVD), hot-wire CVD (HWCVD, also known as cat-CVD, in which a hot wire serves as an energy source for the deposition process), radicals incorporated CVD, and combinations thereof. Exemplary ALD methods include thermal ALD, plasma enhanced ALD (PEALD), spatial isolation ALD, hot-wire ALD (HWALD), radicals incorporated ALD, and combinations thereof. Super critical fluid deposition may also be used. The deposition method is preferably ALD, spatial ALD, or PE-ALD to provide suitable step coverage and film thickness control. The disclosed Ti-containing film forming compositions are particularly suitable for ALD processes because their thermal stability enables perfect self-limited growth.

The disclosed Ti-containing film forming composition may be supplied either neat or may further comprise a suitable solvent, such as C1-C16 hydrocarbons, C1-C16 halogenated hydrocarbons, ketones, ethers, glymes, esters, tetrahydrofurans, dimethyl oxalate (DMO), and combinations thereof. The C1-C16 hydrocarbons and the C1-C16 halogenated hydrocarbons may be saturated or unsaturated. Exemplary solvents include but are not limited to tetrahydrofuran, DMO, ethyl benzene, xylene, mesitylene, decane, and/or dodecane. The adduct may also be used as a solvent when the Ti-containing film forming composition is introduced into the reactor via direct liquid injection. One of ordinary skill in the art will recognize that the adduct is not a suitable solvent for bubblers because it will evaporate prior to vaporization of the Ti halide-containing precursor (i.e., there will be no vapor of the Ti halide-containing precursor in the vapor of the adduct solvent when introduced into the reactor via bubbler due to the differences in vapor pressure between the two). The disclosed Ti halide-containing precursors may be present in varying concentrations in the solvent. The difference between the boiling point of the Ti-halide containing precursor and that of the solvent should range from approximately 0° C. to approximately 80° C.

While the precursors are ideally liquids and vaporized in bubblers or direct liquid injection systems, the use of solid precursors for ALD and CVD precursor vaporization is also possible using sublimators such as ones disclosed in PCT Publication WO2009/087609 to Xu et al. Alternatively, solid precursors may be mixed or dissolved in a solvent to reach a usable melting point and viscosity for usage by Direct Liquid Injection systems.

The neat or blended Ti-containing film forming compositions are introduced into a reactor in vapor form by conventional means, such as tubing and/or flow meters. The vapor form may be produced by vaporizing the neat or blended composition through a conventional vaporization step such as direct vaporization, distillation, or by bubbling, or by using a sublimator such as the one disclosed in PCT Publication WO2009/087609 to Xu et al. The composition may be fed in a liquid state to a vaporizer where it is vaporized before it is introduced into the reactor.

Alternatively, the composition may be vaporized by passing a carrier gas into a container containing the compound or by bubbling the carrier gas into the compound. The carrier gas may include, but is not limited to, Ar, He, $N_2$, and mixtures thereof. Bubbling with a carrier gas may also remove any dissolved oxygen present in the neat or blended compound solution. The carrier gas and vapor form of the composition are then introduced into the reactor as a vapor.

If necessary, the container may be heated to a temperature that permits the composition to be in its liquid phase and to have a sufficient vapor pressure. The container may be maintained at temperatures in the range of, for example, approximately 50° C. to approximately 180° C. Those skilled in the art recognize that the temperature of the container may be adjusted in a known manner to control the amount of composition vaporized. Preferably, the container is maintained at a temperature that results in the Ti-containing film forming composition having a viscosity ranging from approximately 1 to approximately 50 cps, preferably between approximately 1 to approximately 20 cps. Such viscosities make the Ti-containing film forming compositions suitable for introduction into the reactor using direct liquid injection.

Figure 2:
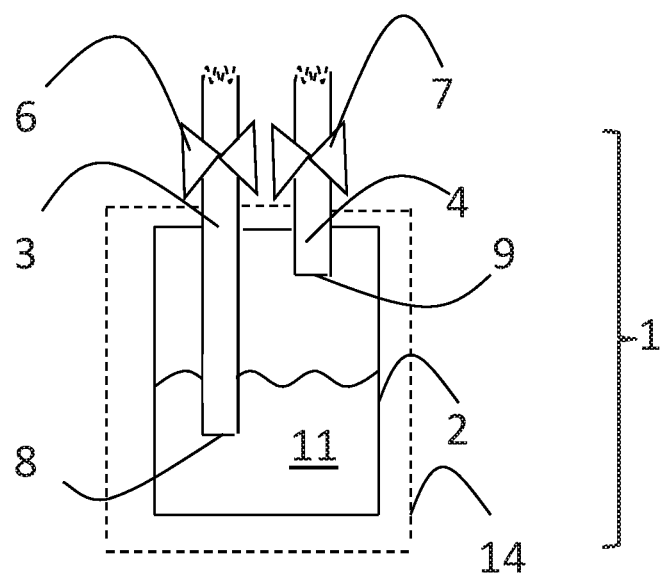
FIG. 2 is a side view of a second embodiment of the Ti-containing film forming composition delivery device 1.

The Ti-containing film forming compositions may be delivered to a semiconductor processing tool by the disclosed Ti-containing film forming composition delivery devices. FIGS. 1 and 2 show two embodiments of the disclosed delivery devices 1.

FIG. 1 is a side view of one embodiment of the Ti-containing film forming composition delivery device 1. In FIG. 1, the disclosed Ti-containing film forming composition 11 is contained within a container 2 having at least two conduits, an inlet conduit 3 and an outlet conduit 4. One of ordinary skill in the precursor art will recognize that the container 2, inlet conduit 3, and outlet conduit 4 are manufactured to prevent the escape of the gaseous form of the Ti-containing film forming composition 11, even at elevated temperature and pressure.

Suitable valves include spring-loaded or tied diaphragm valves. The valve may further comprise a restrictive flow orifice (RFO). The delivery device 1 should be connected to a gas manifold and in an enclosure. The gas manifold should permit the safe evacuation and purging of the piping that may be exposed to air when the delivery device 1 is replaced so that any residual amount of the material does not react.

The delivery device 1 must be leak tight and be equipped with valves that do not permit escape of even minute amounts of the material when closed. The delivery device 1 fluidly connects to other components of the semiconductor processing tool, such as the gas cabinet disclosed above, via valves 6 and 7. Preferably, the container 2, inlet conduit 3, valve 6, outlet conduit 4, and valve 7 are typically made of 316L EP stainless steel.

In FIG. 1, the end 8 of inlet conduit 3 is located above the surface of the Ti-containing film forming composition 11, whereas the end 9 of the outlet conduit 4 is located below the surface of the Ti-containing film forming composition 11. In this embodiment, the Ti-containing film forming composition 11 is preferably in liquid form. An inert gas, including but not limited to nitrogen, argon, helium, and mixtures thereof, may be introduced into the inlet conduit 3. The inert gas pressurizes the container 2 so that the liquid Ti-containing film forming composition 11 is forced through the outlet conduit 4 and to components in the semiconductor processing tool (not shown). The semiconductor processing tool may include a vaporizer which transforms the liquid Ti-containing film forming composition 11 into a vapor, with or without the use of a carrier gas such as helium, argon, nitrogen or mixtures thereof, in order to deliver the vapor to a chamber where a wafer to be repaired is located and treatment occurs in the vapor phase. Alternatively, the liquid Ti-containing film forming composition 11 may be delivered directly to the wafer surface as a jet or aerosol.

FIG. 2 is a side view of a second embodiment of the Ti-containing film forming composition delivery device 1. In FIG. 2, the end 8 of inlet conduit 3 is located below the surface of the Ti-containing film forming composition 11, whereas the end 9 of the outlet conduit 4 is located above the surface of the Ti-containing film forming composition 11. FIG. 2 also includes an optional heating element 14, which may increase the temperature of the Ti-containing film forming composition 11. The Ti-containing film forming composition 11 may be in solid or liquid form. An inert gas, including but not limited to nitrogen, argon, helium, and mixtures thereof, is introduced into the inlet conduit 3. The inert gas flows through the Ti-containing film forming composition 11 and carries a mixture of the inert gas and vaporized Ti-containing film forming composition 11 to the outlet conduit 4 and to the components in the semiconductor processing tool.

Both FIGS. 1 and 2 include valves 6 and 7. One of ordinary skill in the art will recognize that valves 6 and 7 may be placed in an open or closed position to allow flow through conduits 3 and 4, respectively. In another alternative, the inlet conduit 3 and outlet conduit 4 may both be located above the surface of the Ti-containing film forming composition 11 without departing from the disclosure herein. Furthermore, inlet conduit 3 may be a filling port.

Figure 7:
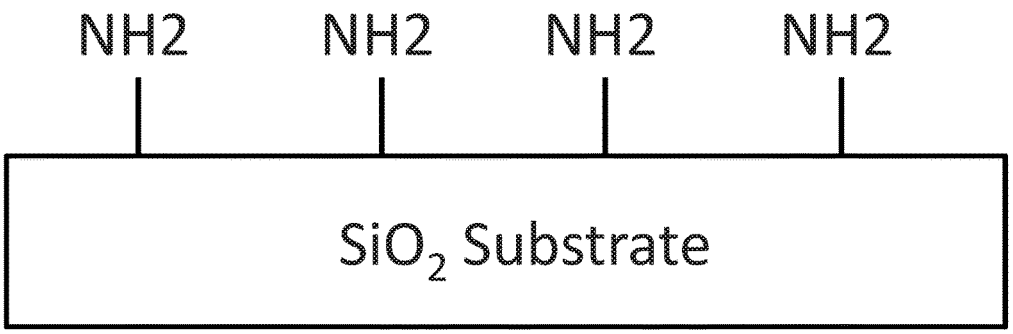
FIG. 7 is a schematic side view of the NH₂ terminated substrate produced by Step 1 of FIG. 6.

In another alternative, either delivery device 1 in FIG. 1 or 2, or a simpler delivery device having a single conduit terminating above the surface of any solid or liquid present, may be used if the Ti-containing film forming composition 11 is in vapor form or if sufficient vapor pressure is present above the solid/liquid phase. In this case, the Ti-containing film forming composition 11 is delivered in vapor form through the conduit 3 or 4 simply by opening the valve 6 in FIG. 1 or 7 in FIG. 2, respectively. The delivery device 1 may be maintained at a suitable temperature to provide sufficient vapor pressure for the Ti-containing film forming composition 11 to be delivered in vapor form, for example by the use of an optional heating element 14.

Figure 3:
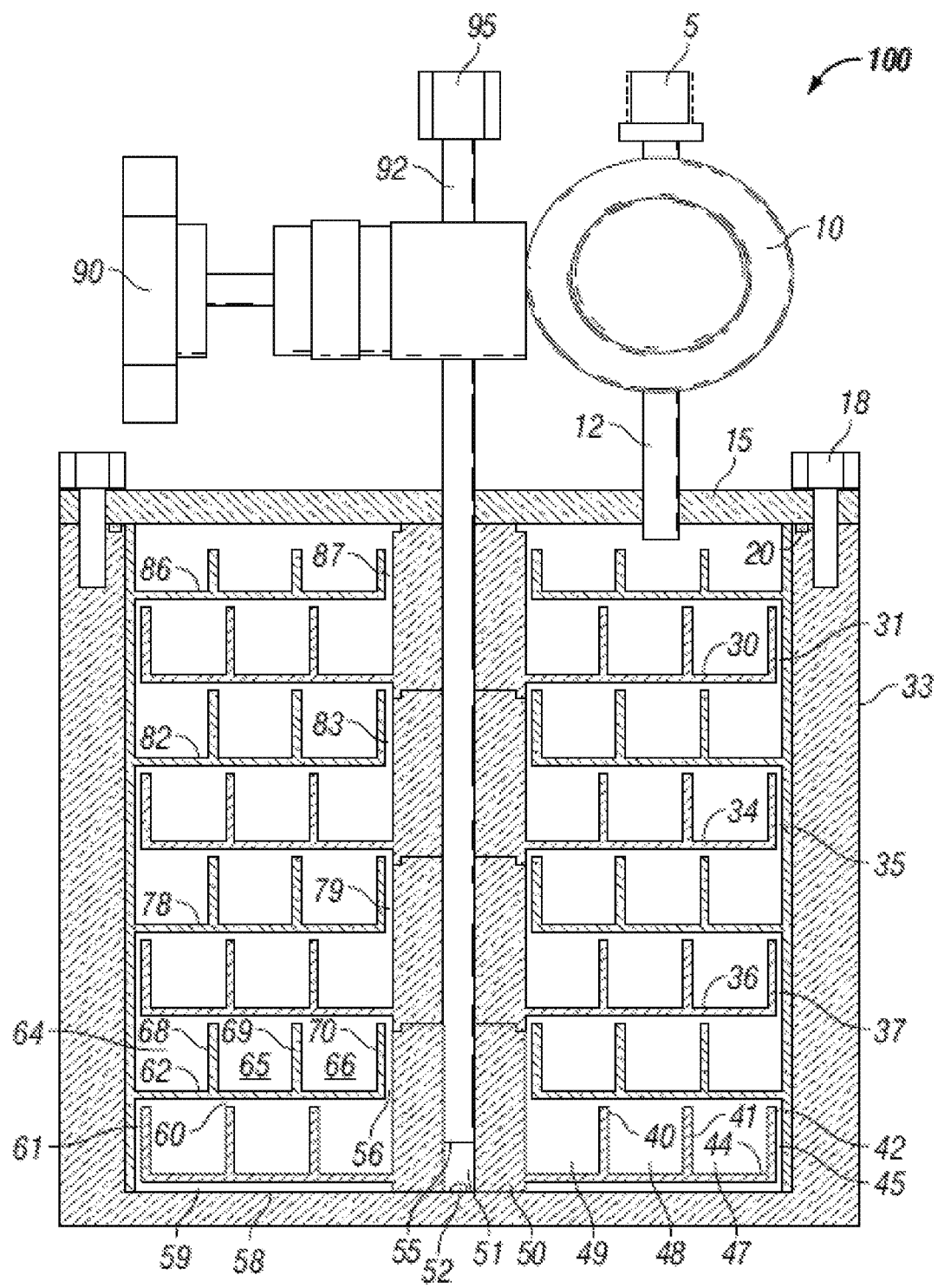
FIG. 3 is an exemplary embodiment of a solid precursor sublimator 100 for subliming solid Ti-containing film forming compositions.

When the Ti-containing film forming compositions are solids, their vapors may be delivered to the reactor using a sublimator. FIG. 3 shows one embodiment of a suitable sublimator 100. The sublimator 100 comprises a container 33. Container 33 may be a cylindrical container, or alternatively, may be any shape, without limitation. The container 33 is constructed of materials such as stainless steel, nickel and its alloys, quartz, glass, and other chemically compatible materials, without limitation. In certain instances, the container 33 is constructed of another metal or metal alloy, without limitation. In certain instances, the container 33 has an internal diameter from about 8 centimeters to about 55 centimeters and, alternatively, an internal diameter from about 8 centimeters to about 30 centimeters. As understood by one skilled in the art, alternate configurations may have different dimensions.

Container 33 comprises a sealable top 15, sealing member 18, and gasket 20. Sealable top 15 is configured to seal container 33 from the outer environment. Sealable top 15 is configured to allow access to the container 33. Additionally, sealable top 15 is configured for passage of conduits into container 33. Alternatively, sealable top 15 is configured to permit fluid flow into container 33. Sealable top 15 is configured to receive and pass through a conduit comprising a dip tube 92 to remain in fluid contact with container 33. Dip tube 92 having a control valve 90 and a fitting 95 is configured for flowing carrier gas into container 33. In certain instances, dip tube 92 extends down the center axis of container 33. Further, sealable top 15 is configured to receive and pass through a conduit comprising outlet tube 12. The carrier gas and vapor of the Ti-containing film forming composition is removed from container 33 through the outlet tube 12. Outlet tube 12 comprises a control valve 10 and fitting 5. In certain instances, outlet tube 12 is fluidly coupled to a gas delivery manifold, for conducting carrier gas from the sublimator 100 to a film deposition chamber.

Container 33 and sealable top 15 are sealed by at least two sealing members 18; alternatively, by at least about four sealing members. In certain instance, sealable top 15 is sealed to container 33 by at least about eight sealing members 18. As understood by one skilled in the art, sealing member 18 releasably couples sealable top 15 to container 33, and forms a gas resistant seal with gasket 20. Sealing member 18 may comprise any suitable means known to one skilled in the art for sealing container 33. In certain instances, sealing member 18 comprises a thumbscrew.

As illustrated in FIG. 3, container 33 further comprises at least one disk disposed therein. The disk comprises a shelf, or horizontal support, for solid material. In certain embodiments, an interior disk 30 is disposed annularly within the container 33, such that the disk 30 includes an outer diameter or circumference that is less than the inner diameter or circumference of the container 33, forming an opening 31. An exterior disk 86 is disposed circumferentially within the container 33, such that the disk 86 comprises an outer diameter or circumference that is the same, about the same, or generally coincides with the inner diameter of the container 33. Exterior disk 86 forms an opening 87 disposed at the center of the disk. A plurality of disks is disposed within container 33. The disks are stacked in an alternating fashion, wherein interior disks 30, 34, 36, 44 are vertically stacked within the container with alternating exterior disks 62, 78, 82, 86. In embodiments, interior disks 30, 34, 36, 44 extend annularly outward, and exterior disks 62, 78, 82, 86 extend annularly toward the center of container 33. As illustrated in the embodiment of FIG. 3, interior disks 30, 34, 36, 44 are not in physical contact with exterior disks 62, 78, 82, 86.

The assembled sublimator 100 comprises interior disks 30, 34, 36, 44 comprising aligned and coupled support legs 50, interior passage 51, concentric walls 40, 41, 42, and concentric slots 47, 48, 49. The interior disks 30, 34, 36, 44 are vertically stacked, and annularly oriented about the dip tube 92. Additionally, the sublimator comprises exterior disks 62, 78, 82, 86. As illustrated in FIG. 3, the exterior disks 62, 78, 82, 86 should be tightly fit into the container 33 for a good contact for conducting heat from the container 33 to the disks 62, 78, 82, 86. Preferably, the exterior disks 62, 78, 82, 86 are coupled to, or in physical contact with, the inner wall of the container 33.

As illustrated, exterior disks 62, 78, 82, 86 and interior disks 30, 34, 36, 44 are stacked inside the container 33. When assembled in container 33 to form sublimator 100, the interior disks 30, 34, 36, 44 form outer gas passages 31, 35, 37, 45 between the assembled exterior disks 62, 78, 82, 86. Further, exterior disks 62, 78, 82, 86 form inner gas passages 56, 79, 83, 87 with the support legs of the interior disks 30, 34, 36, 44. The walls 40, 41, 42 of interior disks 30, 34, 36, 44 form the grooved slots for holding solid precursors. Exterior disks 62, 78, 82, 86 comprise walls 68, 69, 70 for holding solid precursors. During assembly, the solid precursors are loaded into the annular slots 47, 48, 49 of interior disks 30, 34, 36, 44 and annular slots 64, 65, 66 of exterior disks 62, 78, 82, 86.

While FIG. 3 discloses one embodiment of a sublimator capable of delivering the vapor of any solid Ti-containing film forming composition to the reactor, one of ordinary skill in the art will recognize that other sublimator designs may also be suitable, without departing from the teachings herein. Finally, one of ordinary skill in the art will recognize that the disclosed Ti-containing film forming composition 11 may be delivered to semiconductor processing tools using other delivery devices, such as the ampoules disclosed in WO 2006/059187 to Jurcik et al., without departing from the teachings herein.

The reaction chamber may be any enclosure or chamber of a device in which deposition methods take place, such as, without limitation, a parallel-plate type reactor, a cold-wall type reactor, a hot-wall type reactor, a single-wafer reactor, a multi-wafer reactor, or other such types of deposition systems. All of these exemplary reaction chambers are capable of serving as an ALD reaction chamber. The reaction chamber may be maintained at a pressure ranging from about 0.5 mTorr to about 20 Torr, preferably between about 0.1 Torr and about 5 Torr. In addition, the temperature within the reaction chamber may range from about 50° C. to about 600° C. One of ordinary skill in the art will recognize that the optimal deposition temperature range for each Ti halide-containing precursors may be determined experimentally to achieve the desired result.

The reactor contains one or more substrates onto which the thin films will be deposited. A substrate is generally defined as the material on which a process is conducted. The substrates may be any suitable substrate used in semiconductor, photovoltaic, flat panel, or LCD-TFT device manufacturing. Examples of suitable substrates include wafers, such as silicon, SiGe, silica, glass, or Ge. Plastic substrates, such as poly(3,4-ethylenedioxythiophene)poly (styrenesulfonte) [PEDOT:PSS], may also be used. The substrate may also have one or more layers of differing materials already deposited upon it from a previous manufacturing step. For example, the wafers may include silicon layers (crystalline, amorphous, porous, etc.), silicon oxide layers, silicon nitride layers, silicon oxy nitride layers, carbon doped silicon oxide (SiCOH) layers, or combinations thereof. Additionally, the wafers may include copper, cobalt, ruthenium, tungsten and/or other metal layers (e.g. platinum, palladium, nickel, ruthenium, or gold). The wafers may include barrier layers or electrodes, such as tantalum, tantalum nitride, etc. Plastic layers, such as poly(3,4-ethylenedioxythiophene)poly (styrenesulfonate) [PEDOT:PSS] may also be used. The layers may be planar or patterned. The substrate may be an organic patterned photoresist film. The substrate may include layers of oxides which are used as dielectric materials in MIM, DRAM, or FeRam technologies (for example, $ZrO_2$ based materials, $HfO_2$ based materials, $TiO_2$ based materials, rare earth oxide based materials, ternary oxide based materials, etc.) or from nitride-based films (for example, TaN, TiN, NbN) that are used as electrodes. The disclosed processes may deposit the Ti-containing layer directly on the wafer or directly on one or more than one (when patterned layers form the substrate) of the layers on top of the wafer. Furthermore, one of ordinary skill in the art will recognize that the terms "film" or "layer" used herein refer to a thickness of some material laid on or spread over a surface and that the surface may be a trench or a line. Throughout the specification and claims, the wafer and any associated layers thereon are referred to as substrates. The actual substrate utilized may also depend upon the specific precursor embodiment utilized. In many instances though, the preferred substrate utilized will be those that suffer damage from the presence of chlorine in $TiCl_4$, such as titanium oxide, tungsten metal, or GeSbTe layers.

The disclosed processes may selectively deposit the Ti-containing film, particularly when the Ti-containing film forming composition is exposed to a substrate made of multiple different materials. For example, blocking agents such as self-assembling monolayers (SAM) may prevent the adsorption of the Ti halide-containing precursor on a portion of the substrate. The SAMs prevent growth of the Ti-containing film on specific areas, or types, of substrate. Alternatively, or in addition, a free inhibitor may be added during the deposition process to prevent adsorption of the Ti halide-containing precursor on a portion of the substrate. In some cases, the adduct liberated from the Ti-containing film forming composition may deposit on certain surfaces and inhibit growth of the Ti-containing film on such surfaces. For instance, S-containing adducts may bind to copper and prevent growth of the Ti-containing film on copper. In other cases, $TiX_4$ may etch certain metallic surfaces, such as Al. As a result, the Ti-containing film may not grow on these surfaces. A selective deposition process may also result from any combination of these physical phenomena. As a result, one of ordinary skill in the art will recognize that specific Ti-containing film forming compositions will have different reactivates with different substrates.

The temperature and the pressure within the reactor are held at conditions suitable for vapor depositions. In other words, after introduction of the vaporized composition into the chamber, conditions within the chamber are such that at least part of the vaporized Ti halide-containing precursor is deposited onto the substrate to form a Ti-containing film. For instance, the pressure in the reactor may be held between about 1 Pa and about $10^5$ Pa, more preferably between about 25 Pa and about $10^3$ Pa, as required per the deposition parameters. Likewise, the temperature in the reactor may be held between about 100° C. and about 500° C., preferably between about 200° C. and about 450° C. One of ordinary skill in the art will recognize that "at least part of the vaporized Ti halide-containing precursor is deposited" means that some or all of the precursor reacts with or adheres to the substrate.

The temperature of the reactor may be controlled by either controlling the temperature of the substrate holder or controlling the temperature of the reactor wall. Devices used to heat the substrate are known in the art. The reactor wall may be heated to a sufficient temperature to obtain the desired film at a sufficient growth rate and with desired physical state and composition. A non-limiting exemplary temperature range to which the reactor wall may be heated includes from approximately 100° C. to approximately 500° C. When a plasma deposition process is utilized, the deposition temperature may range from approximately 50° C. to approximately 400° C. Alternatively, when a thermal process is performed, the deposition temperature may range from approximately 200° C. to approximately 450° C.

In addition to the disclosed Ti-containing film forming composition, a reactant may also be introduced into the reactor. The reactant may be an oxygen-containing gas such as one of $O_2$, $O_3$, $H_2O$, $H_2O_2$, NO, $N_2O$, $NO_2$, an alcohol (such as ethanol or methanol), a diol (such as ethylene glycol or hydrated hexafluoroacetone), oxygen containing radicals such as O. or OH., NO, $NO_2$, carboxylic acids, formic acid, acetic acid, propionic acid, and mixtures thereof. Preferably, the oxidizing gas is selected from the group consisting of $O_2$, $O_3$, $H_2O$, $H_2O_2$, oxygen containing radicals thereof such as O. or OH., and mixtures thereof.

Alternatively, the reactant may be $H_2$, $NH_3$, hydrazines (such as $N_2H_4$, $MeHNNH_2$, $Me_2NNH_2$, MeHNNHMe, phenyl hydrazine), organic amines (such as $NMeH_2$, $NEtH_2$, $NMe_2H$, $NEt_2H$, $NMe_3$, $NEt_3$, $(SiMe_3)_2NH$, cyclic amines like pyrrolidine or pyrimidine), nitriles (such as acetonitrile), diamines (such as ethylene diamine, dimethylethylene diamine, tetramethylethylene diamine), aminoalcohols (such as ethanolamine [HO—$CH_2$—$CH_2$—$NH_2$], bis ethanolamine [HN($C_2H_5OH)_2$] or tris ethanolamine[N($C_2H_5OH)_3$]), pyrazoline, pyridine, radicals thereof, or mixtures thereof. Preferably the reactant is $H_2$, $NH_3$, radicals thereof, or mixtures thereof.

In another alternative, the reactant may be $N(SiH_3)_3$; $N(SiH_xR_{3-x})_3$, with each x independently 1-3 and each R independently alkyl or $NR'_2$, with each R' independently H or C1-C4 alkyl (such as $(H_3Si)_2N(SiH_2NEt_2)$, $(H_3Si)_2N(SiH_2NiPr_2)$, or $(H_3Si)_2N(SiH_2iPr)$); $R_3Si$—NH—$SiR_3$, with each R independently H, Cl, Br, I, or a C1-C4 alkyl group (such as $H_3Si$—NH—$SiH_3$, $H_2ISi$—NH—$SiH_3$, or $Me_3Si$—NH—$SiMe_3$); hydridosilanes (such as $SiH_4$, $Si_2H_6$, $Si_3H_8$, $Si_4H_{10}$, $Si_5H_{10}$, $Si_6H_{12}$); chlorosilanes and chloropolysilanes (such as $SiHCl_3$, $SiH_2Cl_2$, $SiH_3Cl$, $Si_2Cl_6$, $Si_2HCl_5$, $Si_3Cl_8$); bromosilanes and bromopolysilanes (such as $SiHBr_3$, $SiH_2Br_2$, $SiH_3Br$, $Si_2Br_6$, $Si_2HBr_5$, $Si_3Br_8$); iodosilanes and iodopolysilanes (such as $SiHI_3$, $SiH_2I_2$, $SiH_3I$, $Si_2I_6$, $Si_2HI_5$, $Si_3I_8$); alkylsilanes (such as $Me_2SiH_2$, $Et_2SiH_2$, $MeSiH_3$, $EtSiH_3$); and aminosilanes (such as tris(dimethylamino)silane, bis(diethylamino)silane, di-isopropylaminosilane and other mono, bis or tris aminosilanes);

radicals thereof; or mixtures thereof. Preferably, the reactant is $(SiH_3)_3N$ or an aminosilane, such as bis(diethylamino)silane.

The reactant may be treated by a plasma, in order to decompose the reactant into its radical form. $N_2$ may also be utilized as a reducing gas when treated with plasma. For instance, the plasma may be generated with a power ranging from about 50 W to about 2500 W, preferably from about 100 W to about 400 W. The plasma may be generated or present within the reactor itself. Alternatively, the plasma may generally be at a location removed from the reactor, for instance, in a remotely located plasma system. One of skill in the art will recognize methods and apparatus suitable for such plasma treatment.

For example, the reactant may be introduced into a direct plasma reactor, which generates plasma in the reaction chamber, to produce the plasma-treated reactant in the reaction chamber. Exemplary direct plasma reactors include the Titan™ PECVD System produced by Trion Technologies. The reactant may be introduced and held in the reaction chamber prior to plasma processing. Alternatively, the plasma processing may occur simultaneously with the introduction of the reactant. In-situ plasma is typically a 13.56 MHz RF inductively coupled plasma that is generated between the showerhead and the substrate holder. The substrate or the showerhead may be the powered electrode depending on whether positive ion impact occurs. Typical applied powers in in-situ plasma generators are from approximately 30 W to approximately 1000 W. Preferably, powers from approximately 30 W to approximately 600 W are used in the disclosed methods. More preferably, the powers range from approximately 100 W to approximately 500 W. The disassociation of the reactant using in-situ plasma is typically less than achieved using a remote plasma source for the same power input and is therefore not as efficient in reactant disassociation as a remote plasma system, which may be beneficial for the deposition of Ti-containing films on substrates easily damaged by plasma.

Alternatively, the plasma-treated reactant may be produced outside of the reaction chamber. The MKS Instruments' ASTRONi® reactive gas generator may be used to treat the reactant prior to passage into the reaction chamber. Operated at 2.45 GHz, 7 kW plasma power, and a pressure ranging from approximately 0.5 Torr to approximately 10 Torr, the reactant $O_2$ may be decomposed into two O. radicals. Preferably, the remote plasma may be generated with a power ranging from about 1 kW to about 10 kW, more preferably from about 2.5 kW to about 7.5 kW.

The vapor deposition conditions within the chamber allow the disclosed Ti-containing film forming composition and the reactant to react and form a Ti-containing film on the substrate. In some embodiments, Applicants believe that plasma-treating the reactant may provide the reactant with the energy needed to react with the disclosed composition.

Depending on what type of film is desired to be deposited, an additional precursor compound may be introduced into the reactor. The precursor may be used to provide additional elements to the Ti-containing film. The additional elements may include lanthanides (e.g., Ytterbium, Erbium, Dysprosium, Gadolinium, Praseodymium, Cerium, Lanthanum, Yttrium), germanium, silicon, aluminum, boron, phosphorous, hafnium, zirconium, a Group 3 element (i.e., Sc, Y, La, or $A_c$), or a Group 5 element (i.e., V, Nb, or Ta), or mixtures of these. When an additional precursor compound is utilized, the resultant film deposited on the substrate contains Ti in combination with at least one additional element.

When the resulting film contains Al, suitable reactants include trialkylaluminum (e.g., $AlMe_3$, $AlEt_3$, etc.), dialkylaluminum halide (e.g., $AlMe_2Br$, $AlEt_2Br$, etc.), alkylaluminum dihalide (e.g., $AlMeBr_2$, $AlEtBr_2$, etc.), alkylamino or alkoxy derivatives of aluminum (e.g., $Al(NEt_2)_3$, $Al(OtBu)_3$, etc.), alanes, amine-adducted alanes (e.g., $Al:NEt_3$), and mixtures thereof. The resulting amorphous TiAl film may be used for micromirror arrays in complementary metal oxide semiconductors (CMOS). Schmidt et al., J. of Micro/Nanolithography, MEMS, and MOEMS, 7(2) 2008. Vapor deposition of the amorphous TiAl film provides better conformality, surface smoothness, compositional uniformity, and in general fewer defects than those produced by sputtering.

The Ti-containing film forming compositions and reactants may be introduced into the reactor either simultaneously (chemical vapor deposition), sequentially (atomic layer deposition) or different combinations thereof. The reactor may be purged with an inert gas between the introduction of the composition and the introduction of the reactant. Alternatively, the reactant and the composition may be mixed together to form a reactant/compound mixture, and then introduced to the reactor in mixture form. Another example is to introduce the reactant continuously and to introduce the Ti-containing film forming composition by pulse (pulsed chemical vapor deposition).

The vaporized composition and the reactant may be pulsed sequentially or simultaneously (e.g. pulsed CVD) into the reactor. Each pulse of composition may last for a time period ranging from about 0.01 seconds to about 100 seconds, alternatively from about 0.3 seconds to about 30 seconds, alternatively from about 0.5 seconds to about 10 seconds. The reactant may also be pulsed into the reactor. In such embodiments, the pulse of each gas may last from about 0.01 seconds to about 100 seconds, alternatively from about 0.3 seconds to about 30 seconds, alternatively from about 0.5 seconds to about 10 seconds. In another alternative, the vaporized composition and one or more reactants may be simultaneously sprayed from a shower head under which a susceptor holding several wafers is spun (spatial ALD).

Depending on the particular process parameters, deposition may take place for a varying length of time. Generally, deposition may be allowed to continue as long as desired or necessary to produce a film with the necessary properties. Typical film thicknesses may vary from several angstroms to several hundreds of microns, depending on the specific deposition process. The deposition process may also be performed as many times as necessary to obtain the desired film.

In one non-limiting exemplary CVD type process, the vapor phase of the disclosed Ti-containing film forming composition and a reactant are simultaneously introduced into the reactor. The two react to form the resulting Ti-containing thin film. When the reactant in this exemplary CVD process is treated with a plasma, the exemplary CVD process becomes an exemplary PECVD process. The reactant may be treated with plasma prior or subsequent to introduction into the chamber.

In one non-limiting exemplary ALD type process, the vapor phase of the disclosed Ti-containing film forming composition is introduced into the reactor, where the Ti halide-containing precursor physi- or chemisorbs on the substrate. Excess composition may then be removed from the reactor by purging and/or evacuating the reactor. A desired gas (for example, $O_3$) is introduced into the reactor where it reacts with the physi- or chemisorped precursor in a self-limiting manner. Any excess reducing gas is removed from the reactor by purging and/or evacuating the reactor. If the desired film is a Ti metal film, this two-step process may provide the desired film thickness or may be repeated until a film having the necessary thickness has been obtained.

Alternatively, if the desired film contains the Ti metal and a second element, the two-step process above may be followed by introduction of the vapor of an additional precursor compound into the reactor. The additional precursor compound will be selected based on the nature of the Ti metal film being deposited. After introduction into the reactor, the additional precursor compound is contacted with the substrate. Any excess precursor compound is removed from the reactor by purging and/or evacuating the reactor. Once again, a desired gas may be introduced into the reactor to react with the precursor compound. Excess gas is removed from the reactor by purging and/or evacuating the reactor. If a desired film thickness has been achieved, the process may be terminated. However, if a thicker film is desired, the entire four-step process may be repeated. By alternating the provision of the Ti-containing compound, additional precursor compound, and reactant, a film of desired composition and thickness can be deposited.

When the reactant in this exemplary ALD process is treated with a plasma, the exemplary ALD process becomes an exemplary PEALD process. The reactant may be treated with plasma prior or subsequent to introduction into the chamber.

In a second non-limiting exemplary ALD type process, the vapor phase of one of the disclosed Ti halide-containing precursors, for example $TiBr_4:S(nPr)_2$, is introduced into the reactor, where it is contacted with a TiO substrate. Excess Ti halide-containing precursor may then be removed from the reactor by purging and/or evacuating the reactor. A desired gas (for example, $NH_3$) is introduced into the reactor where it reacts with the absorbed Ti halide-containing precursor in a self-limiting manner to form a TiN film. Any excess N-containing gas is removed from the reactor by purging and/or evacuating the reactor. These two steps may be repeated until the TiN film obtains a desired thickness.

The Ti-containing films resulting from the processes discussed above may include a titanium oxide ($Ti_nO_m$, wherein each n and m is an integer which inclusively ranges from 1 to 6), such as $TiO_2$; a titanium nitride, such as TiN or TiSiN; a titanium oxide containing another element M ($TiM_iO_x$, wherein i ranges from 0.1 to 1; x ranges from 1 to 6; and M is selected from zirconium, hafnium, a Group 3 element, a Group 5 element, a lanthanide, Si, Al, B, P or Ge); or a titanium oxynitride ($TiM'_iN_yO_x$, wherein i ranges from 0 to 1; x and y range from 1 to 6; and M' is selected from hafnium, zirconium, a Group 3 element, a Group 5 element, a lanthanide, Si, Al, B, P or Ge). One of ordinary skill in the art will recognize that by judicial selection of the appropriate disclosed compound, optional precursor compounds, and reactant species, the desired film composition may be obtained.

The Ti-containing film forming composition may be used to deposit Ti on a silicon layer and annealed to form a $TiSi_2$ layer. Alternatively, the Ti-containing film forming composition and a Si-containing reactant, such as TSA, may be used to form a $TiSi_2$ layer. In either alternative, the $TiSi_2$ layer formed preferably exhibits C54 polymorphism and a resistivity between approximately 10 $_u\Omega cm$ and approximately 20 $_u\Omega cm$, preferably between approximately 13 $_u\Omega cm$ and approximately 16 $_u\Omega cm$. Alternatively, if a higher resistivity is desired, a C49 polymorphic $TiSi_2$ layer may be formed. The C49 polymorphic $TiSi_2$ layer has a resistivity between approximately 60 $_u\Omega cm$ and approximately 70 $_u\Omega cm$. The polymorphic phase may be determined using XRD.

The Ti-containing films resulting from the processes discussed above contain between approximately 0 atomic % to approximately 5 atomic % of C; between approximately 0 atomic % to approximately 40 atomic % of O; between approximately 0 atomic % to approximately 2 atomic % of S; between approximately 0 atomic % to approximately 2 atomic % of Se; between approximately 0 atomic % to approximately 2 atomic % of Te; or between approximately 0 atomic % to approximately 2 atomic % of P impurities (depending on the adduct composition).

Upon obtaining a desired film thickness, the film may be subject to further processing, such as thermal annealing, furnace-annealing, rapid thermal annealing, UV or e-beam curing, and/or plasma gas exposure. Those skilled in the art recognize the systems and methods utilized to perform these additional processing steps. For example, the Ti-containing film may be exposed to a temperature ranging from approximately 200° C. and approximately 1000° C. for a time ranging from approximately 0.1 second to approximately 7200 seconds under an inert atmosphere, a H-containing atmosphere, a N-containing atmosphere, an O-containing atmosphere, or combinations thereof. Most preferably, the temperature is 400° C. for 3600 seconds under a H-containing atmosphere or an O-containing atmosphere. The resulting film may contain fewer impurities and therefore may have an improved density resulting in improved leakage current. The annealing step may be performed in the same reaction chamber in which the deposition process is performed. Alternatively, the substrate may be removed from the reaction chamber, with the annealing/flash annealing process being performed in a separate apparatus. Any of the above post-treatment methods, but especially thermal annealing, has been found effective to reduce carbon and nitrogen contamination of the Ti-containing film. This in turn tends to improve the resistivity of the film.

EXAMPLES

The following examples illustrate experiments performed in conjunction with the disclosure herein. The examples are not intended to be all inclusive and are not intended to limit the scope of disclosure described herein.

Due to its hygroscopic nature, the $TiX_4$ reactants and $TiX_n:L_y$ adducts were all handled in a glove box under dried inert atmosphere. The various Lewis base ligands were dried and stored under argon using standard drying techniques, such as molecular sieves or other desiccant treatment.

Example 1: Synthesis of $TiBr_4:S(nPr)_2$ 0.5 g of solid $TiBr_4$ was reacted with 1 molar equivalent of $S(nPr)_2$ in a glove box. An exotherm and immediate color change to dark red was observed. Almost no solid particles remained. After 15 minutes, the mixture was filtered using a syringe plug filter to produce a clear dark red liquid. According to Baker et al., the resulting product is mono-substituted and adopts a penta-coordinated trigonal bipyramidal geometry:

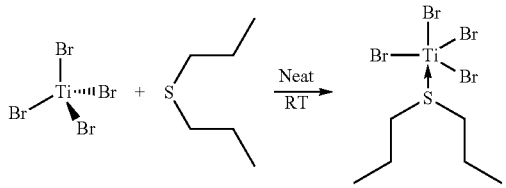

Figure 4:
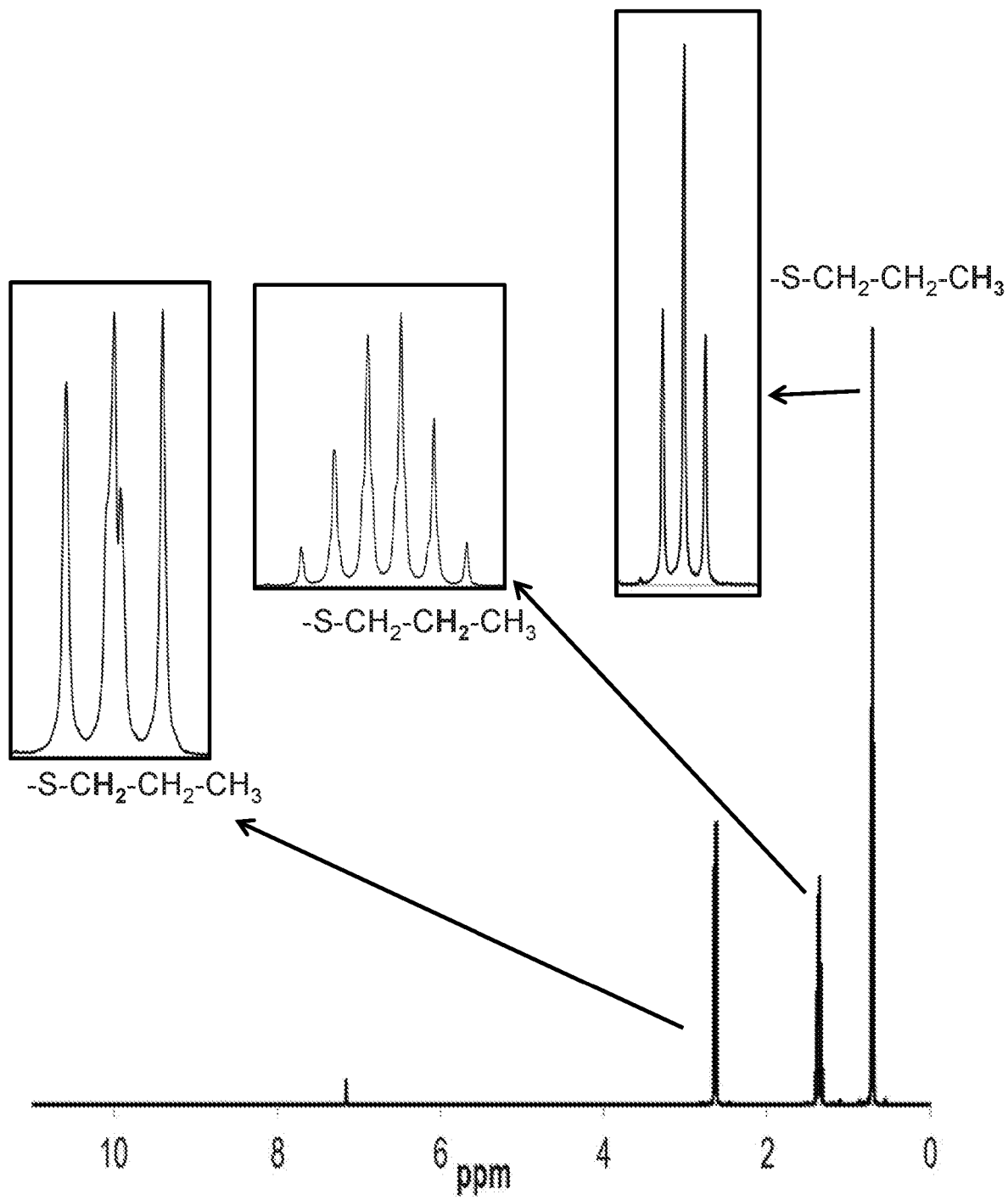
FIG. 4 is the ¹H NMR spectrum of the TiBr₄:S(nPr)₂ precursor produced in Example 1.

FIG. 4 is a $^1$H-NMR spectrum of the resulting product in $C_6D_6$. The clean spectrum shows no impurities. The α-Ti $^1$H splitting suggests magnetic inequivalence of the two propyl groups, which may be due to the restricted conformation of the ligand.

Figure 5:
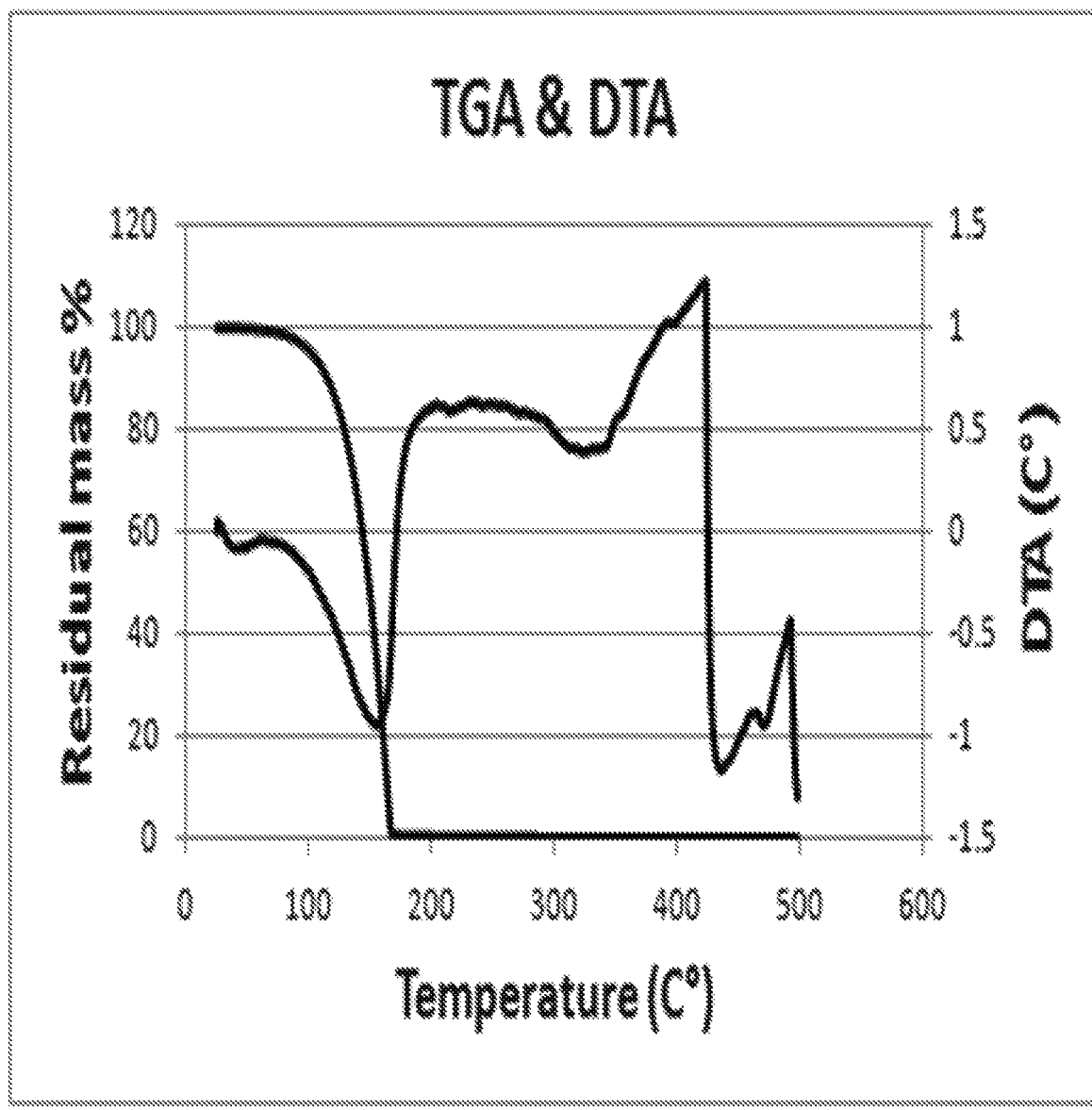
FIG. 5 is a ThermoGravimetric Analysis/Differential Thermal Analysis (TGA/DTA) graph illustrating the percentage of weight loss (TGA) or the differential temperature (DTA) of TiBr₄:S(nPr)₂ upon temperature increase.

FIG. 5 is a ThermoGravimetric Analysis/Differential Thermal Analysis (TGA/DTA) graph illustrating the percentage of weight loss (TGA) or the differential temperature (DTA) of TiBr$_4$:S(nPr)$_2$ in an Al$_2$O$_3$ pan upon temperature increase at 1 atmosphere. The TGA results demonstrate clean evaporation (<0.5% residue). No residue was obtained when the TGA analysis was performed at reduced pressure (~12 Torr).

Example 2: Atomic Layer Deposition (ALD) of TiBr$_4$:S(nPr)$_2$

Figure 6:
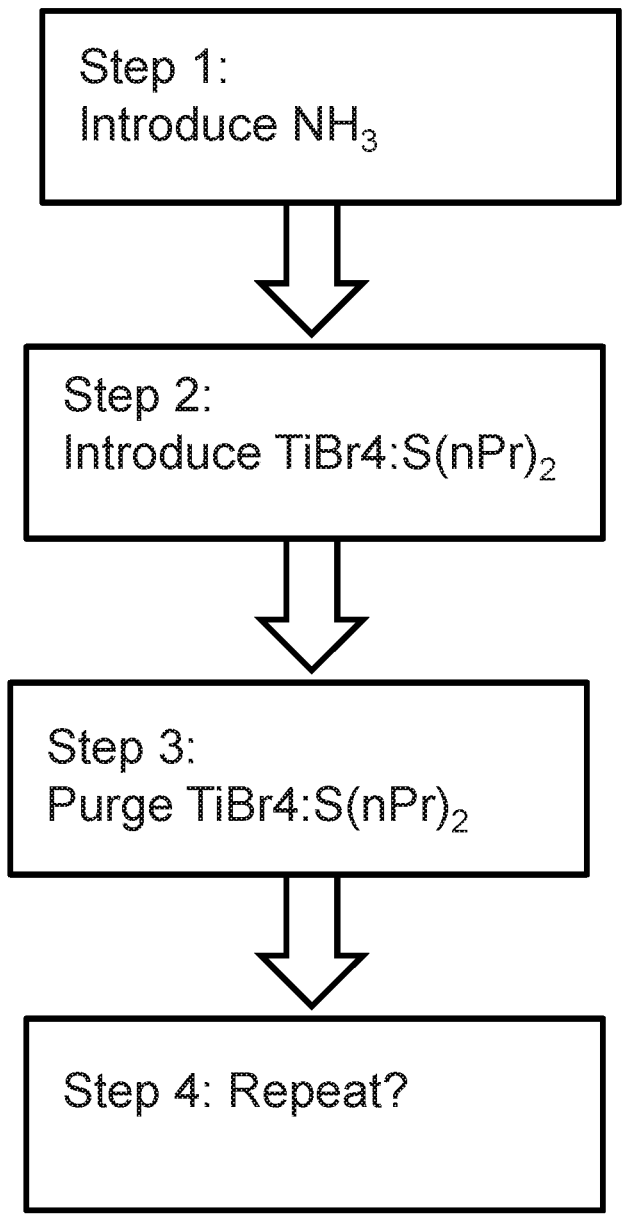
FIG. 6 is a flow chart showing the process of Example 2.

ALD of TiN was performed using the liquid TiBr$_4$:S(nPr)$_2$ prepared in Example 1. FIG. 6 is a flow chart showing the ALD process. In Step 1, a 3 second pulse of NH$_3$ is introduced into a reaction chamber (not shown) containing a SiO$_2$ substrate and reacts with the substrate to produce the NH$_2$-terminated substrate of FIG. 7. The reactor was maintained at 200° C., 300° C., and 400° C. at 1 Torr. The 3 second NH$_3$ pulse is followed by a 10 second Ar purge pulse to remove any excess NH$_3$ or reaction by-products.

Figure 8:
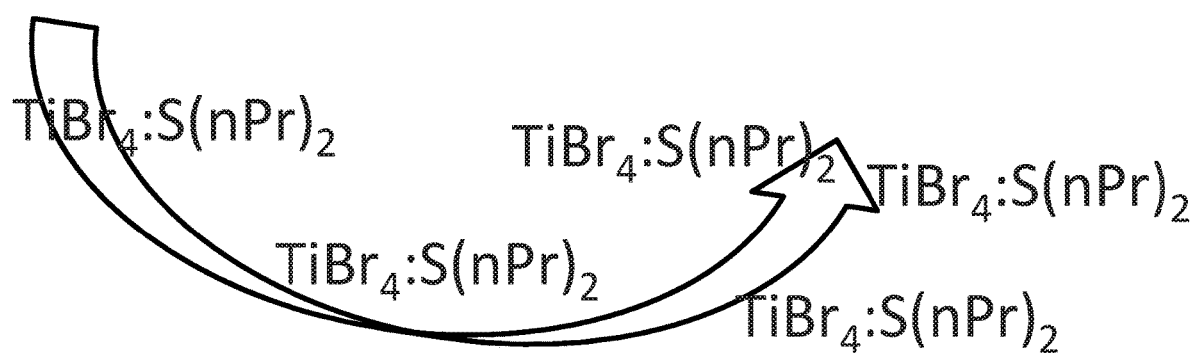
FIG. 8 is a schematic side view of the substrate at the start of Step 2 of FIG. 6.
Figure 8:
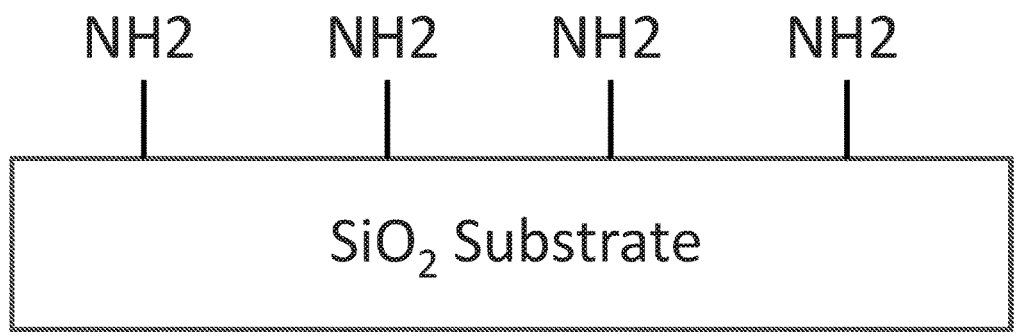
Figure 9:
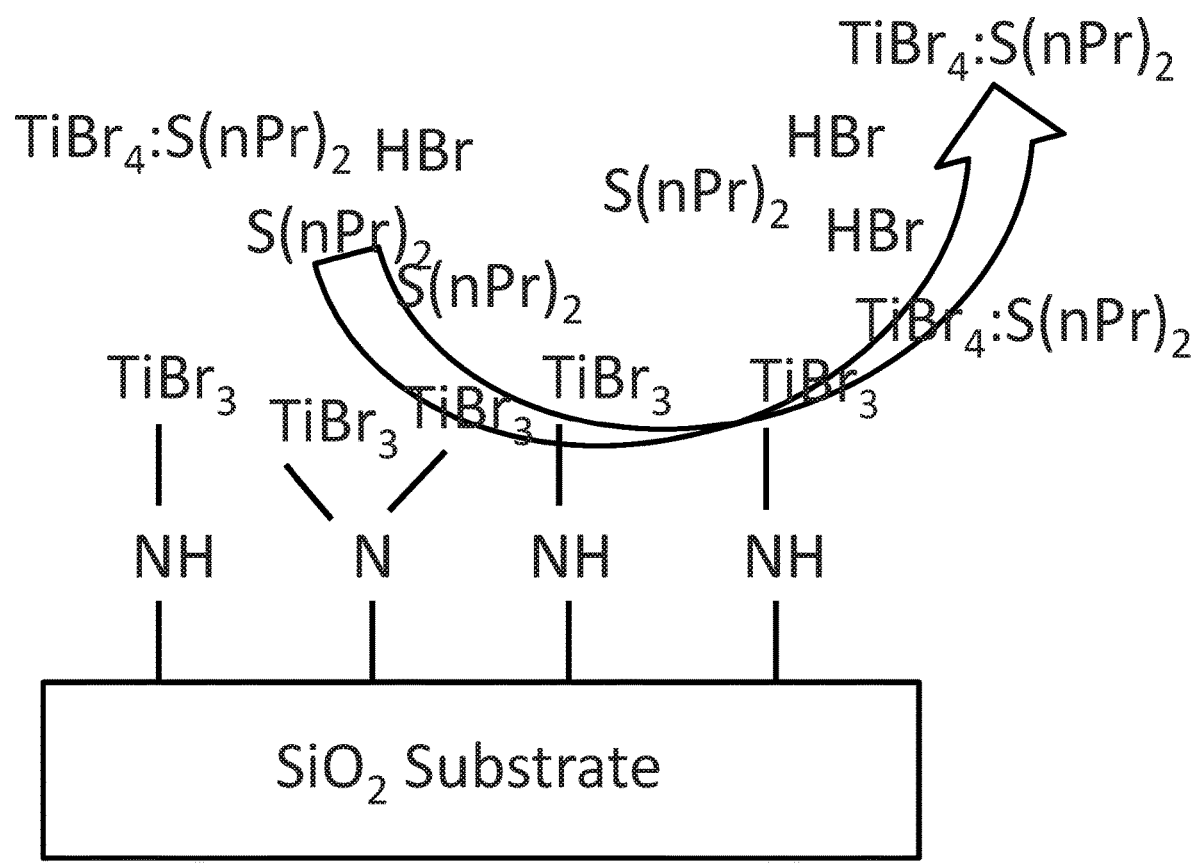
FIG. 9 is a schematic side view of the reactions with the substrate and the reaction by-products produced by Step 2 of FIG. 6.

In Step 2 of FIG. 6, a 6 second pulse of the vapor form of the TiBr$_4$:S(nPr)$_2$ precursor is introduced into a reaction chamber. The liquid TiBr$_4$:S(nPr)$_2$ precursor of Example 1 was placed in a vessel heated and maintained at 72° C. to produce the vapor form. The vessel utilized a cross flow configuration, in which the ends of the inlet conduit and outlet conduit were both located above the surface of the Ti-containing film forming composition. FIG. 8 is a schematic side view of the substrate at the start of Step 2. FIG. 9 is a schematic side view of the reaction between the TiBr$_4$:S(nPr)$_2$ precursor with the substrate as well as the reaction by-products, such as HBr and S(nPr)$_2$. The S(nPr)$_2$ reaction by-product is produced by cleavage of the S(nPr)$_2$ adduct from the TiBr$_4$:S(nPr)$_2$ precursor. The HBr reaction by-product is produced by the reaction between the —NH$_2$ substrate surface and one Br of the TiBr$_4$:S(nPr)$_2$ precursor.

Figure 10:
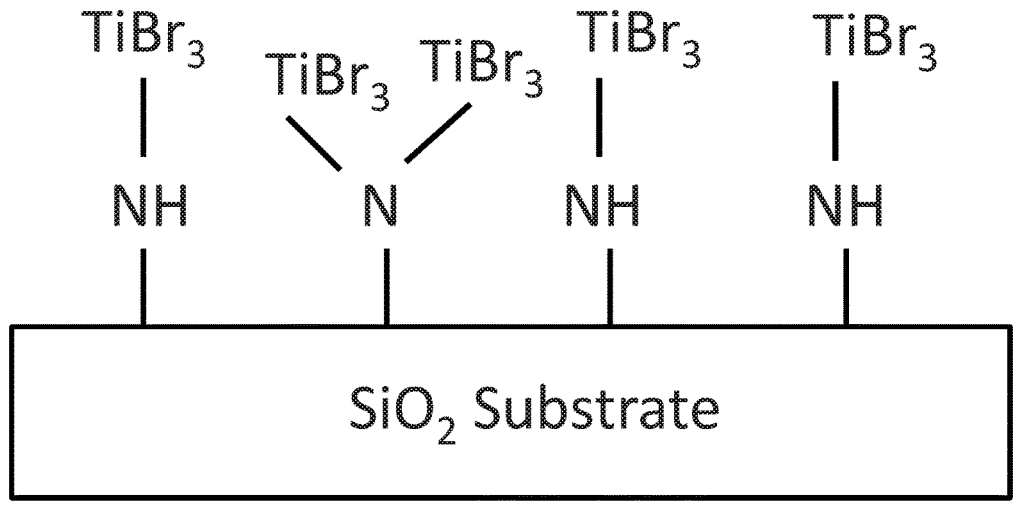
FIG. 10 is schematic side view of the substrate produced by Step 3 of FIG. 6.

In Step 3 of FIG. 6, a ten second argon pulse purges any excess TiBr$_4$:S(nPr)$_2$ precursor and reaction by-products from the reaction chamber to produce the substrate of FIG. 10.

Figure 11:
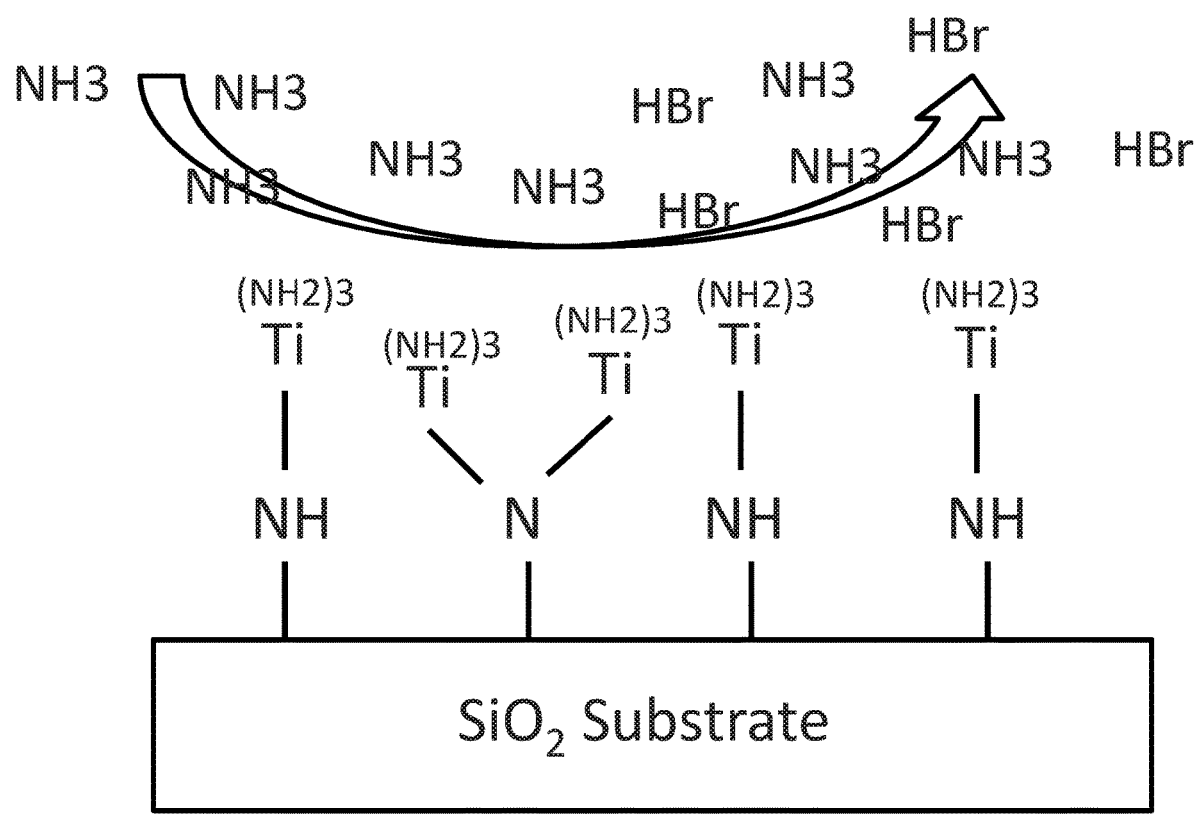
FIG. 11 is a schematic side view of the substrate during Step 4 of FIG. 6.

In Step 4 of FIG. 6, the process may be repeated if the desired film thickness has not been obtained by introducing the 3 second NH$_3$ pulse of Step 1. FIG. 11 is a schematic side view of the reaction between the substrate of FIG. 10 with the NH$_3$ reactant of Step 1 of FIG. 6, as well as the reaction by-products, such as HBr. The HBr reaction by-product is produced by reaction of one Br of the TiBr$_3$ substrate with one H of the NH$_3$ reactant. The 3 second NH$_3$ pulse is followed by a 10 second Ar purge pulse to remove any excess NH$_3$ or reaction by-products.

ALD saturation behavior was observed at 400° C. with a growth rate of 0.57 Å/cycle on silicon dioxide substrate (SiO$_2$). 74% step coverage was obtained after 300 cycles on a feature having a 1:20 aspect ratio.

Figure 12:
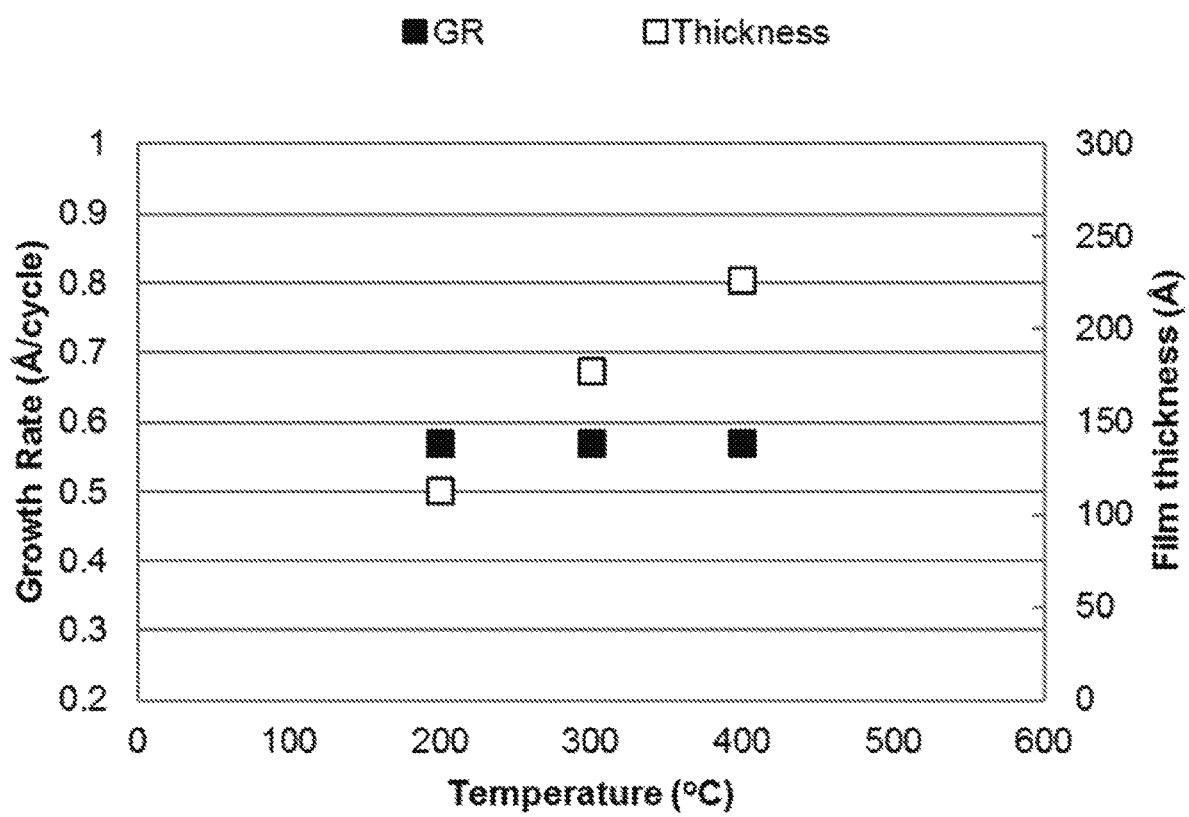
FIG. 12 is a graph showing the titanium nitride film growth rate and resulting titanium nitride film thickness per number of ALD cycles using the TiBr₄:S(nPr)₂ precursor.

FIG. 12 is a graph demonstrating (a) the growth rate and (b) film thickness of TiN thin films using TiBr$_4$:S(nPr)$_2$/NH$_3$ as a function of the substrate temperature between 200 and 400° C. Linear growth was observed.

The stoichiometry of some TiN films was analysed by XPS (X ray Photoelectron Spectroscopy). However, the films contained a large amount of oxygen. The oxygen may have been the result of handling the films under atmosphere after completion of the deposition process. Nonetheless, the Ti:N ratio of the films was approximately 1:1.

Comparative Example

Comparative ALD of TiN was performed using solid TiBr$_4$. TiBr$_4$ was placed in a vessel heated and maintained at 55° C. The reactor was maintained at 200° C., 300° C., and 500° C. at 0.5 Torr. Length of TiBr$_4$ introduction, argon purge, NH$_3$ introduction, and argon purge was 3 seconds, 10 seconds, 2 seconds, and 10 seconds, respectively. ALD saturation behavior was observed at 300° C. and 500° C. with a growth rate of 0.57 and 056 Å/cycle, respectively, on silicon wafer (Si). 74.5% step coverage was obtained after 200 cycles on a feature having a 1:20 aspect ratio.

As can be seen, the ALD results using the liquid TiBr$_4$:S(nPr)$_2$ precursor were similar to those obtained using the solid TiBr$_4$ precursor. However, the liquid TiBr$_4$:S(nPr)$_2$ precursor is much easier to handle than the solid TiBr$_4$ precursor.

It will be understood that many additional changes in the details, materials, steps, and arrangement of parts, which have been herein described and illustrated in order to explain the nature of the invention, may be made by those skilled in the art within the principle and scope of the invention as expressed in the appended claims. Thus, the present invention is not intended to be limited to the specific embodiments in the examples given above and/or the attached drawings.

We claim:

1. A titanium-containing film forming composition comprising a titanium bromide-containing precursor having one of the following formula:

$$TiX_b:A_c$$

with b=3 or 4; c=1-3; X=Br; A=SR$_2$, SeR$_2$, TeR$_2$, or PR$_3$, and each R is independently H or a C1-C5 hydrocarbon, wherein the Ti bromide-containing precursor is a liquid at standard temperature and pressure.

2. The titanium-containing film forming composition of claim 1, further comprising a mixture of TiBr$_2$(=O), TiBr$_3$(OH)), and TiO$_2$.

3. The titanium-containing film forming composition of claim 2, further comprising hydrogen bromide.

4. The titanium-containing film forming composition of claim 1, further comprising a mixture of TiI$_2$(=O), TiI$_3$(OH), and TiO$_2$.

5. The titanium-containing film forming composition of claim 1, further comprising hydrogen iodide.

6. The titanium-containing film forming composition of claim 1, wherein A is SR$_2$.

7. The titanium-containing film forming composition of claim 6, wherein each R is independently a C1-C2 hydrocarbon when c=2.

8. The titanium-containing film forming composition of claim 6, wherein the Ti halide-containing precursor being $TiBr_4:S(nPr)_2$.

9. The titanium-containing film forming composition of claim 6, further comprising $TiX_4:SR'_2$, wherein each R' is independently H or a C1-C5 hydrocarbon and R'≠R.

10. The titanium-containing film forming composition of claim 1, wherein A is $SeR_2$.

11. The titanium-containing film forming composition of claim 1, wherein A is $TeR_2$.

12. The titanium-containing film forming composition of claim 1, wherein A is $PR_3$.

13. The titanium-containing film forming composition of claim 1, further comprising a hydrocarbon solvent or of free adduct.

14. The titanium-containing film forming composition of claim 1, further comprising $H_2O$.

15. A method of depositing a Ti-containing film on a substrate, the method comprising introducing the Ti-containing film forming composition of claim 1 into a reactor containing the substrate and depositing at least part of the Ti bromide-containing precursor onto the substrate to form the Ti-containing film.

16. The method of claim 15, further comprising introducing a reactant into the reactor.

17. The method of claim 15, wherein the Ti-containing film is selectively deposited onto the substrate.

\* \* \* \* \*